US009714265B2

(12) United States Patent
Essigmann et al.

(10) Patent No.: US 9,714,265 B2
(45) Date of Patent: Jul. 25, 2017

(54) MUTAGENIC NUCLEOSIDE ANALOGS AND USES THEREOF

(71) Applicant: Massachusetts Institute of Technology, Cambridge, MA (US)

(72) Inventors: John M. Essigmann, Cambridge, MA (US); Andrei Tokmakoff, Evanston, IL (US); Bogdan I. Fedeles, Cambridge, MA (US); Vipender Singh, Cambridge, MA (US); Chunte Peng, Mountain View, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/009,628

(22) Filed: Jan. 28, 2016

(65) Prior Publication Data

US 2016/0222050 A1 Aug. 4, 2016

Related U.S. Application Data

(60) Provisional application No. 62/109,020, filed on Jan. 28, 2015.

(51) Int. Cl.

| | | |
|---|---|---|
| *A01N 43/04* | (2006.01) | |
| *A61K 31/70* | (2006.01) | |
| *C07H 19/12* | (2006.01) | |
| *A61K 31/7052* | (2006.01) | |
| *A61K 31/706* | (2006.01) | |
| *A61K 31/7076* | (2006.01) | |
| *A61K 31/708* | (2006.01) | |
| *C07H 19/04* | (2006.01) | |
| *C07H 19/173* | (2006.01) | |
| *C07H 19/23* | (2006.01) | |
| *C12Q 1/68* | (2006.01) | |
| *G01N 21/3577* | (2014.01) | |
| *G01N 33/15* | (2006.01) | |
| *A61K 31/7068* | (2006.01) | |
| *A61K 31/7064* | (2006.01) | |

(52) U.S. Cl.
CPC .......... *C07H 19/12* (2013.01); *A61K 31/706* (2013.01); *A61K 31/708* (2013.01); *A61K 31/7052* (2013.01); *A61K 31/7076* (2013.01); *C07H 19/04* (2013.01); *C07H 19/173* (2013.01); *C07H 19/23* (2013.01); *C12Q 1/6811* (2013.01); *G01N 21/3577* (2013.01); *G01N 33/15* (2013.01); *A61K 31/7064* (2013.01); *A61K 31/7068* (2013.01)

(58) Field of Classification Search
None
See application file for complete search history.

(56) References Cited

U.S. PATENT DOCUMENTS

2014/0206639 A1 7/2014 Essigmann et al.

FOREIGN PATENT DOCUMENTS

| GB | 2415431 | 12/2005 |
|---|---|---|
| WO | WO 03/018030 A1 | 3/2003 |
| WO | WO 2004/028454 A2 | 4/2004 |

OTHER PUBLICATIONS

Li et al., Tautomerism provides a molecular explanation for the mutagenic properties of the anti-HIV nucleoside 5-aza-5,6-dihydro-2'-deoxycytidine. Proc Natl Acad Sci U S A. Aug. 12, 2014;111(32):E3252-9. doi: 10.1073/pnas.1405635111. Epub Jul. 28, 2014.

*Primary Examiner* — Patrick Lewis
(74) *Attorney, Agent, or Firm* — Wolf, Greenfield & Sacks, P.C.

(57) ABSTRACT

The present disclosure provides nucleoside analogs of Formula (I) or (II). The nucleoside analogs are expected to show multiple tautomerism and may increase the mutation of an RNA and/or DNA (be mutagenic) of a virus or cancer cell. The multiple tautomerism and mutagenesis of the nucleoside analogs may be adjusted by substituting the nucleoside analogs with one or more electron-donating groups and/or electron-withdrawing groups to increase or decrease the $pK_a$ (e.g., to a $pK_a$ between 5.5 or 8.5). The present disclosure also provides pharmaceutical compositions and kits including the nucleoside analogs and methods of treating a viral infection (e.g., influenza, HIV infection, or hepatitis) or cancer using the nucleoside analogs, pharmaceutical compositions, or kits.

32 Claims, 7 Drawing Sheets

Figure 4A
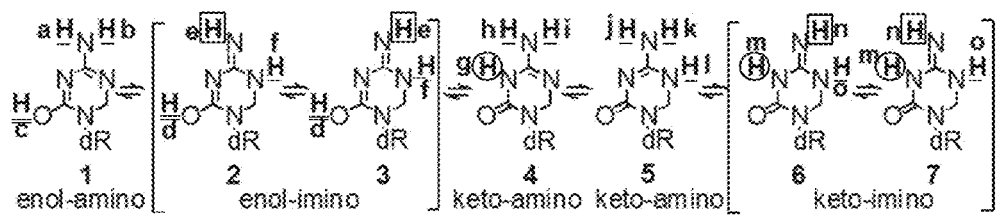
Figure 4B
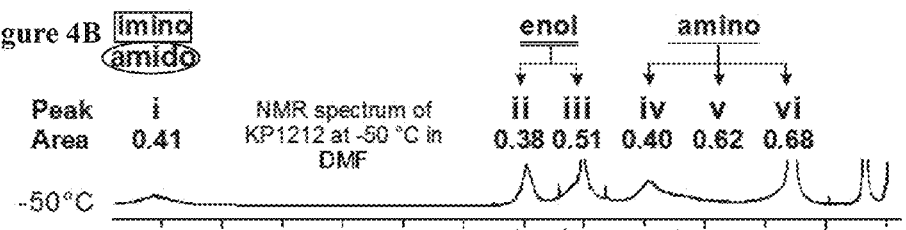
Figure 4C
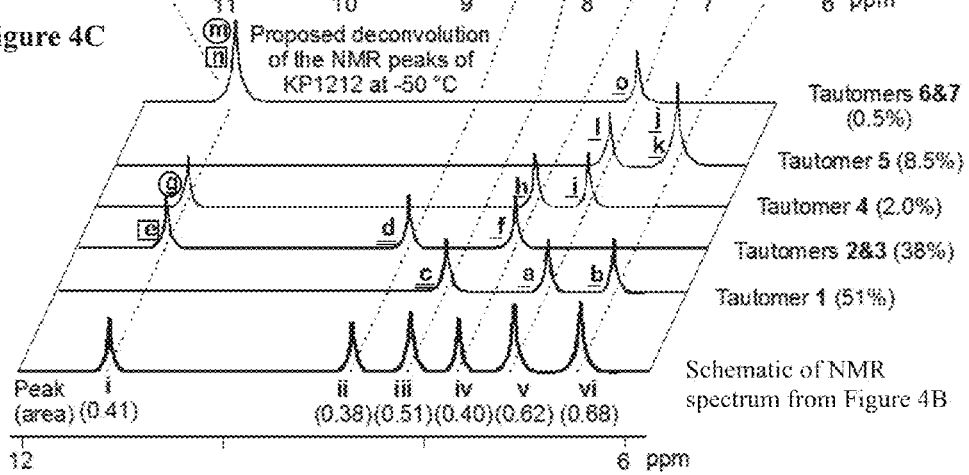
Figure 4D

BIE = 0.984 ± 0.004

MUTAGENIC NUCLEOSIDE ANALOGS AND USES THEREOF

RELATED APPLICATIONS

The present application claims priority under 35 U.S.C. §119(e) to U.S. provisional patent application, U.S. Ser. No. 62/109,020, filed Jan. 28, 2015, the entire contents of which are incorporated herein by reference.

GOVERNMENT SUPPORT

This invention was made with U.S. Government support under grant numbers R37 CA080024, P01 CA026731, and P30 ES002109, awarded by the National Institutes of Health, and under grant number CHE-1212557 awarded by the National Science Foundation. The U.S. Government has certain rights in the invention.

BACKGROUND OF THE INVENTION

A major obstacle for viral disease treatment is viral persistence, which makes many current anti-rival therapies only temporality effective. Using HIV/AIDS as an example, nucleoside/nucleotide analog reverse transcriptase (RT) inhibitors, such as AZT, are the most commonly used drugs for inhibiting HIV reception. However, drug resistance generated by HIV mutations severely reduces the efficacy of those drugs. One reason for drug resistance against these chain terminators is the evolution of the HIV RT under selective pressure by the drug.

An approach, called "lethal mutagenesis" has recently been developed (Loeb et al., *Proc. Natl. Acad. Sci. USA*, 1999, 96, 1492-1497; Mullins et al., PLoS ONE, 2011, 6, e15135; Clay et al., *Journal of the International Association of Physicians in AIDS Care,* 2011, 10, 232-238; Harris et al., *Antiviral Res.* 2005, 67, 1-9). This approach involves nucleotide analogs that can be incorporated into the HIV genome and extended (they are not chain terminators) and increase the mutation rate of HIV. When the mutation rate of HIV is over its "error catastrophe limit," the HIV will produce mostly non-viable progeny. Those nucleotide analogs are thus examples of lethal mutagens. The lethal mutagenesis approach has been shown to be safe by a drug candidate KP1212 (shown below, the active form of the pro-drug KP1461) in Phase I and II clinical trials and offers the possibility of treatment of the persistent population of HIV, which would become increasingly dominated by weak or non-viable viruses. Another molecule currently in clinical trials is compound T705, which is also known to work by lethal mutagenesis.

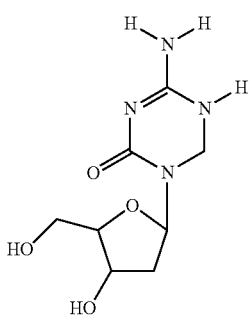

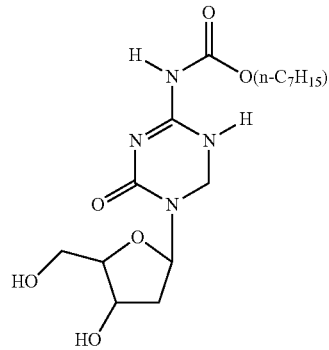

SUMMARY OF THE INVENTION

The present disclosure provides, in one aspect, compounds of Formula (I) or (II). The compounds described herein are nucleoside analogs and are expected to show multiple tautomerism (e.g., being present in at least two different tautomeric forms) and mutagenesis (e.g., lethal mutagenesis) against viruses and cancer cells. It has been surprisingly discovered that the multiple tautomerism and mutagenesis of nucleoside analogs can be adjusted by substituting the nucleoside analogs with one or more electron-donating groups and/or electron-withdrawing groups to increase or decrease the $pK_a$ (acid dissociation constant at logarithmic scale). In some aspects of the disclosure, the $pK_a$ of a nucleobase, nucleoside, nucleotide, or analog thereof, impacts its mutagenicity (e.g., in vivo). In some embodiments, a nucleobase, nucleoside, nucleotide, or analog thereof, having a $pK_a$ of between 5.5 and 8.5 (e.g., between 6 and 8), inclusive, is more mutagenic than an equivalent compound having a higher or lower $pK_a$. Accordingly, in some embodiments, a nucleobase, nucleoside, nucleotide, or analog thereof, is substituted with one or more electron withdrawing and/or electron donating groups to adjust the $pK_a$ to between 5.5 and 8.5 (e.g., between 6 and 8). A compound of Formula (II) may be protonated (e.g., under physiological conditions) to form the corresponding compound of Formula (I). Therefore, a compound of Formula (I) is a protonated form of the corresponding compound of Formula (II). In certain embodiments, a compound of Formula (I) is the active form of the corresponding compound of Formula (II).

In one aspect, the present disclosure provides compounds of Formula (I):

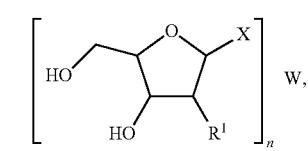

and solvates, hydrates, polymorphs, co-crystals, tautomers, stereoisomers, isotopically labeled derivatives, and prodrugs thereof, wherein:

$R^1$ is H or —OH;

X is of the formula:

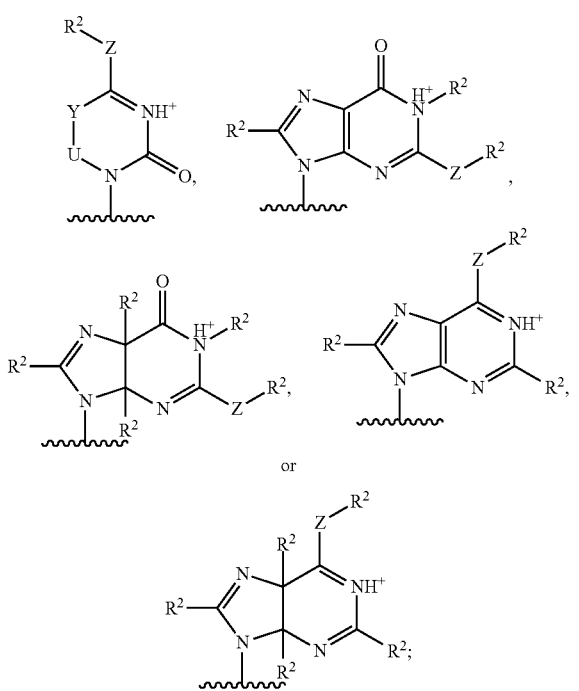

Y is —O—, —NR² — or —C(R²)₂—;
U is —O—, —NR² — or —C(R²)₂—;
Z is —O—, —S—, —NH—, or —C(R²)₂—;
each instance of R² is independently H, an electron-withdrawing group, or an electron-donating group;
W is an anionic counterion; and
n is 1, 2, or 3;
wherein the $pK_a$ of the compound is between 5.5 and 8.5, inclusive, and the $pK_a$ is a $pK_a$ at 25° C.

In certain embodiments, a compound described herein is not KP1212,

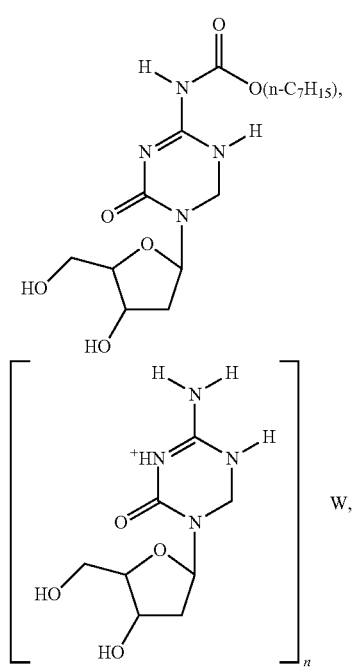

or a pharmaceutically acceptable salt, solvate, hydrate, polymorph, co-crystal, tautomer, or stereoisomer thereof.

In another aspect, the present disclosure provides compounds of Formula (II):

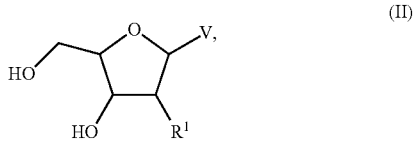

and pharmaceutically acceptable salts, solvates, hydrates, polymorphs, co-crystals, tautomers, stereoisomers, isotopically labeled derivatives, and prodrugs thereof, wherein:
V is of the formula:

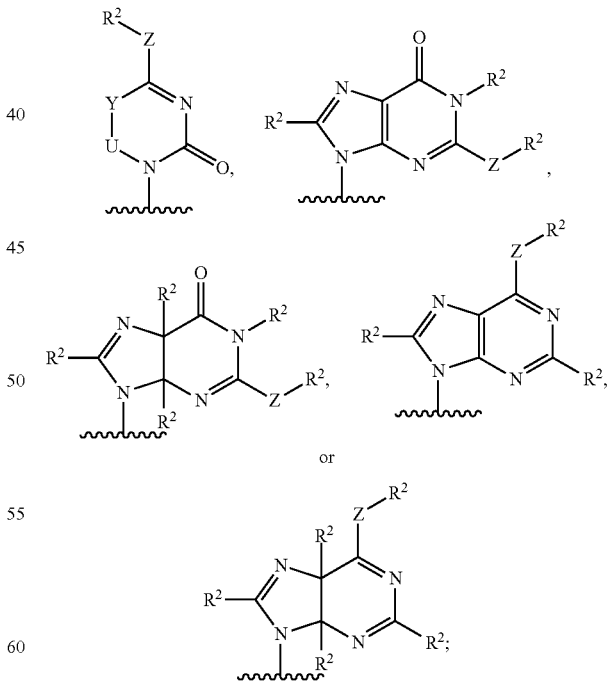

and
R¹, Y, U, Z, and R² are as described herein;
wherein the $pK_a$ of the compound is between 5.5 and 8.5, inclusive, and the $pK_a$ is a $pK_a$ at 25° C.

In another aspect, the present disclosure provides pharmaceutical compositions comprising a compound described herein and optionally a pharmaceutically acceptable excipient.

In another aspect, the present disclosure provides methods of increasing the mutagenicity of a first compound, the methods comprising substituting the first compound with one or more electron donating groups and/or electron withdrawing groups to provide a second compound, wherein:

the first compound is a nucleobase, nucleoside, nucleotide, or an analog thereof; and if the $pK_a$ of the first compound is higher than 7, then the $pK_a$ of the second compound is lower than the $pK_a$ of the first compound; or if the $pK_a$ of the first compound is lower than 7, then the $pK_a$ of the second compound is higher than the $pK_a$ of the first compound;

wherein each $pK_a$ is independently a $pK_a$ at 25° C.

In another aspect, the present disclosure provides methods of determining tautomeric forms of a compound, the methods comprising:

providing the compound in physiological conditions;

performing a variable temperature 1-dimensional infrared spectroscopy test or a variable temperature 2-dimensional infrared spectroscopy test on the compound; and performing a density functional theory calculation on the compound;

wherein the compound is a nucleobase, nucleoside, nucleotide, or an analog thereof.

In another aspect, the present disclosure provides methods of determining tautomeric forms of a compound, the methods comprising:

providing the compound in physiological conditions; and performing a density functional theory calculation on the compound to determine the binding isotope effect for each of the tautomeric forms;

wherein the compound is a nucleobase, nucleoside, nucleotide, or an analog thereof, and interacts non-covalently with a nucleic acid, aptamer, or protein.

In another aspect, the present disclosure provides methods of evaluating the mutagenicity of a compound in different pH conditions, the methods comprising:

a primer extension reaction on a template strand comprising at a defined site a compound to provide a synthesized strand, wherein the primer extension reaction is performed in a solution buffered at pH between 5.0 and 9.0, inclusive, using a recombinant polymerase and a custom designed primer;

specifically polymerase chain reaction (PCR) amplifying the synthesized strand to provide a PCR product; and analyzing the PCR product using a restriction endonuclease and postlabeling (REAP) assay to quantitate the mutagenicity of the compound present in the template strand;

wherein the compound is a nucleobase, nucleoside, nucleotide, or an analog thereof.

In another aspect, the present disclosure provides methods of treating a viral infection in a subject in need thereof, the methods comprising administering to the subject an effective amount of a compound or pharmaceutical composition described herein.

In another aspect, the present disclosure provides methods of increase the mutation rate of a RNA or DNA of a virus, the methods comprising contacting the virus with an effective amount of a compound or pharmaceutical composition described herein.

In another aspect, the present disclosure provides methods of killing a virus, the methods comprising contacting the virus with an effective amount of a compound or pharmaceutical composition described herein.

In another aspect, the present disclosure provides methods of inhibiting the replication of a virus, the methods comprising contacting the virus with an effective amount of a compound or pharmaceutical composition described herein.

In another aspect, the present disclosure provides methods of treating cancer in a subject in need thereof, the methods comprising administering to the subject an effective amount of a compound or pharmaceutical composition described herein.

In another aspect, the present disclosure provides methods of increasing the mutation rate of a RNA and/or DNA of a cancer cell, the methods comprising contacting the cancer cell with an effective amount of a compound or pharmaceutical composition described herein.

In another aspect, the present disclosure provides methods of inducing apoptosis of a cancer cell, the methods comprising contacting the cancer cell with an effective amount of a compound or pharmaceutical composition described herein.

In another aspect, the present disclosure provides methods of decreasing DNA methylation in a cancer cell, the methods comprising contacting the cancer cell with an effective amount of a compound or pharmaceutical composition described herein.

In another aspect, the present disclosure provides kits comprising:

a compound or pharmaceutical composition described herein; and instructions for using the compound or pharmaceutical composition.

DEFINITIONS

Definitions of specific functional groups and chemical terms are described in more detail below. The chemical elements are identified in accordance with the Periodic Table of the Elements, CAS version, *Handbook of Chemistry and Physics*, 75<sup>th</sup> Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5<sup>th</sup> Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3<sup>rd</sup> Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and subrange within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, ethanoate, propanoate, benzoate, glycerate, lactate, tartrate, glycolate, and the like), BF$_4^-$, PF$_4^-$, PF$_6^-$, AsF$_6^-$, SbF$_6^-$, B[3,5-(CF$_3$)$_2$C$_6$H$_3$]$_4^-$, BPh$_4^-$, Al(OC(CF$_3$)$_3$)$_4^-$, and a carborane anion (e.g., CB$_{11}$H$_{12}^-$ or (HCB$_{11}$Me$_5$Br$_6$)$^-$). In certain embodiments, a counterion described herein is F$^-$, Cl$^-$, Br$^-$, I$^-$, NO$_3^-$, ClO$_4^-$, OH$^-$, H$_2$PO$_4^-$, HPO$_4^{2-}$, PO$_4^{3-}$, HSO$_4^-$, SO$_4^{2-}$, OTf$^-$, OTs$^-$, OMs$^-$, OAc$^-$, OBz$^-$, BF$_4^-$, PF$_4^-$, PF$_6^-$, AsF$_6^-$, or SbF$_6^-$.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in

*Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N ($R^{bb}$)$_2$, and —P(=O)(N$R^{bb}$)$_2$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a viral infection or cancer. In some embodiments, treatment may be administered after one or more signs or symptoms of the viral infection or cancer have developed or have been observed. In other embodiments, treatment may be administered in the absence of signs or symptoms of the viral infection or cancer. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a viral infection or cancer but is at risk of developing the viral infection or cancer or who was with a viral infection or cancer, is not with the viral infection or cancer, but is at risk of regression of the viral infection or cancer. In certain embodiments, the subject is at a higher risk of developing the viral infection or cancer or at a higher risk of regression of the viral infection or cancer than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses. In certain embodiments, an effective amount is effective for increasing the mutagenicity of a first compound, determining tautomeric forms of a compound, treating a viral infection in a subject in need thereof, increase the mutation rate of a RNA or DNA of a virus, killing a virus, inhibiting the replication of a virus, treating cancer in a subject in need thereof, increasing the mutation rate of a RNA and/or DNA of a cancer cell, inducing apoptosis of a cancer cell, or decreasing DNA methylation in a cancer cell.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is effective for treating a viral infection in a subject in need thereof. In certain embodiments, a therapeutically effective amount is effective for treating cancer in a subject in need thereof.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for preventing a viral infection.

The term "physiological conditions" refers to conditions of the external or internal milieu that may occur in nature for that organism or cell system, in contrast to artificial laboratory conditions. An aqueous solution, temperature between 20 and 40° C., inclusive (e.g., about 37° C.), pressure of about 1 atmosphere, pH between 6 and 8, inclusive, glucose concentration between 1 and 20 mM, inclusive, atmospheric oxygen concentration, earth gravity, and a combination thereof, are examples of physiological conditions.

BRIEF DESCRIPTION OF THE DRAWINGS

FIG. 1A: pH-dependent (Fourier transform infrared) FTIR spectra of KP1212 from pH* 1.6 (red or thin solid line) to 13.9 (blue or thick solid line) at 25° C. FIG. 1B: populations of protonated, neutral, and deprotonated KP1212 as a function of pH* obtained from the first three components of singular value decomposition (SVD) analysis. The solid lines show fits of the Henderson-Hasselbalch equation with $pK_{a1}$ and $pK_{a2}$. FIGS. 1C to 1E: SVD reconstructed IR spectra representative for the protonated (FIG. 1C), neutral (FIG. 1D), and deprotonated (FIG. 1E) KP1212. The grey curves, labeled A, in FIG. 1C and FIG. 1D are the experimental FTIR spectra of 1-(1',4'-cyclohexadienyl)-2-methylaminopropane (CMP) at pH* 1.6 and 7.4, respectively. The pH* is the pH measured in $D_2O$, as measured with a pH meter. The FTIR experiments were run in $D_2O$.

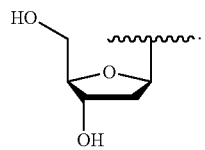

Figure 3:
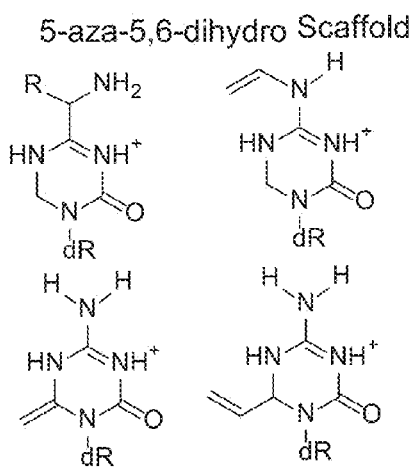
FIG. 3 shows the structures of the cationic portion of exemplary compounds described herein. These compounds are expected to have an altered $pK_a$ compared to their parent compounds and thus to be more mutagenic. These compounds are shown in their protonated (active) form. dR.
Figure 3:
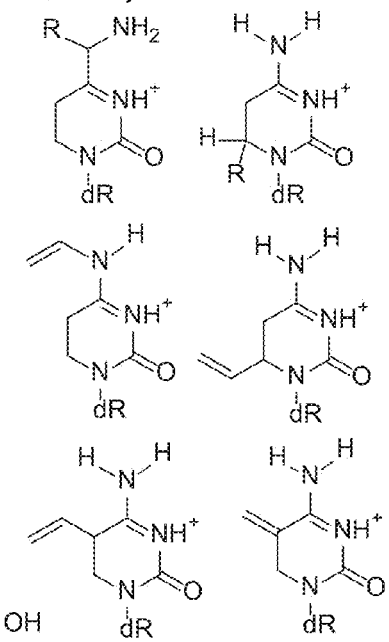
Figure 3:
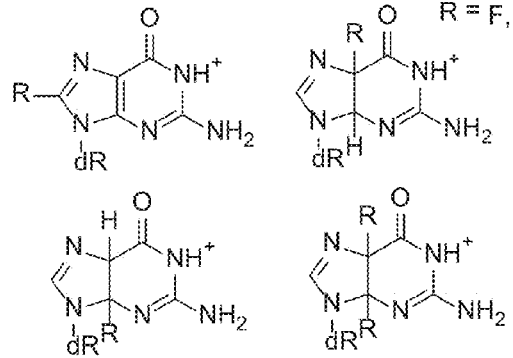
Figure 3:
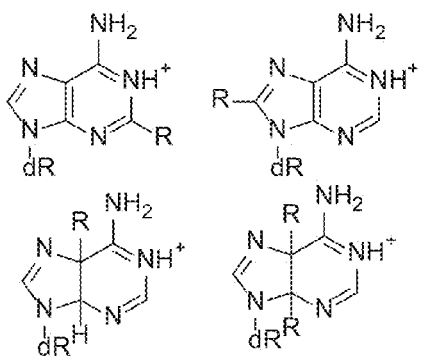

Each of the structures shown in FIG. 3 independently includes an anionic counterion W to maintain electrical neutrality.

FIGS. 4A to 4D show exemplary matrix deconvolution of nuclear magnetic resonance (NMR) spectra to calculate the distribution of the tautomeric forms of a compound described herein. FIG. 4A shows the structures of the seven possible tautomeric structures of KP1212 (2 & 3 and 6 & 7 are geometric isomers of the same tautomeric form). The active protons (a-o) on the nucleobase portion of the molecule are designated with different colors or labels to indicate their chemical environment (type): blue or box (imino), purple or circle (amido), red or double underline (enol), and green or single underline (amino). FIG. 4B shows the $^1H$ NMR spectrum of KP1212 in DMF-$d_7$ at −50° C. (5.5 to 12.0 ppm). The peaks from the active protons on the nucleobase portion are labeled as i to vi and their corresponding areas are indicated. According to their chemical shifts, the type of the active protons on the KP1212 nucleobase that contribute to each peak is indicated. FIG. 4C shows a schematic of the deconvolution process of the $^1H$ NMR spectrum of KP1212 at −50° C. depicting how the active proton peaks corresponding to each tautomer contribute to the overall spectrum. Each of the six peaks identified in the NMR spectrum in FIG. 4B, denoted i to vi, is schematically represented as the bottom trace (in blue or bold). To indicate each tautomer's respective contributions to the six peaks, schematic representations of the NMR signals of the active protons of each tautomer are shown (black or un-bold traces). Each peak is labeled with a colored or labeled letter (a-o), which corresponds to the active protons labeled in FIG. 4A. FIG. 4D shows the mathematical analysis of NMR spectrum using matrix algebra to calculate relative distribution of tautomers. The elements of matrix A represent the number of active protons from each tautomer (columns) that contribute to each of the six NMR peaks (rows). The matrix X elements are the unknown variables, which represent the relative amounts of each tautomer. Matrix B contains the areas corresponding to each peak in the NMR spectrum at −50° C. Linear equations were generated from the matrix equation $A*X=B$. Solving the system of linear equations yielded values for the unknowns, which provided the relative distribution of individual tautomers of KP1212.

Figure 5A:
Figure 5B:
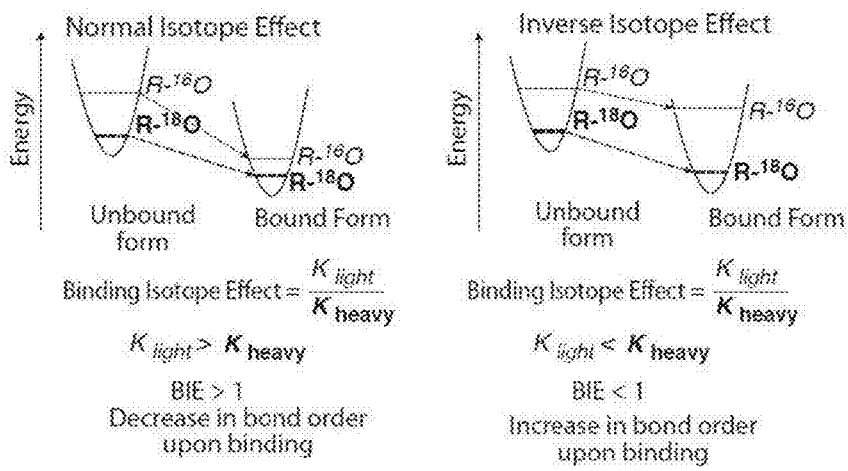
Figure 5B:
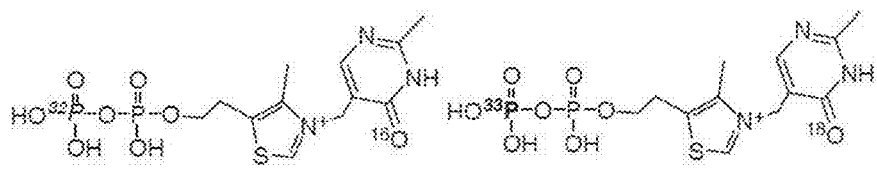

FIGS. 5A and 5B show exemplary binding isotope effect (BIE) for determining the tautomeric forms of a ligand (OxyTPP) bound to its target macromolecule (TPP riboswitch). FIG. 5A shows the physical basis for interpreting $^{18}O$ binding isotope effects. A BIE of less than one indicates increased bond order upon binding of a ligand to its target or tighter binding (or greater stabilization) of the ligand carrying the heavier isotope and vice versa. FIG. 5B: magnitude of $^{18}O$ BIE measured for the binding of OxyTPP to the TPP riboswitch. The inverse value was consistent with the keto tautomer of OxyTPP binding in the pocket of the TPP riboswitch.

DETAILED DESCRIPTION OF CERTAIN EMBODIMENTS OF THE INVENTION

Mutagenic nucleoside analogs, such as the dihydro bases described in U.S. Patent Application Publication, US 2014/0206639, incorporated herein by reference, may be useful in treating viral infections and cancer. In one aspect, the present invention provides compounds of Formula (I), and solvates, hydrates, polymorphs, co-crystals, tautomers, stereoisomers, isotopically labeled derivatives, and prodrugs thereof. In another aspect, the present invention provides compounds of Formula (II), and pharmaceutically acceptable salts, solvates, hydrates, polymorphs, co-crystals, tautomers, stereoisomers, isotopically labeled derivatives, and prodrugs thereof. The compounds described herein are novel nucleoside analogs and are expected to show, e.g., under physiological conditions, multiple tautomerism and lethal mutagenesis against viruses and cancer cells. It has been surprisingly discovered that the multiple tautomerism and mutagenesis of a nucleobase, nucleoside, nucleotide, or analog thereof can be adjusted by substituting the nucleobase, nucleoside, nucleotide, or analog thereof, with one or more electron-donating groups and/or electron-withdrawing groups to increase or decrease the $pK_a$. In some aspects of the disclosure, the $pK_a$ of a nucleobase, nucleoside, nucleotide, or analog thereof, impacts its mutagenicity (e.g., in vivo). In some embodiments, a nucleobase, nucleoside, nucleotide, or analog thereof, having a $pK_a$ of between 5.5 and 8.5 (e.g., between 6 and 8), inclusive, is more mutagenic than an equivalent compound having a higher or lower $pK_a$.

Accordingly, in some embodiments, a nucleobase, nucleoside, nucleotide, or analog thereof, is substituted with one or more electron withdrawing and/or electron donating groups to adjust the $pK_a$ to between 5.5 and 8.5 (e.g., between 6 and 8). Without wishing to be bound by any particular theory, the tautomeric and mutagenic properties of a compound described herein are affected by the $pK_a$ of the compound, and, under physiological conditions, the closer to 7 the $pK_a$ of the compound is, the higher the tautomerism and mutagenicity of the compound are.

Compounds

In certain embodiments, the compound is of the formula:

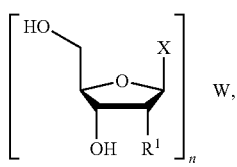

or a solvate, hydrate, polymorph, co-crystal, tautomer, stereoisomer, isotopically labeled derivative, or prodrug thereof.

In certain embodiments, the compound is of the formula:

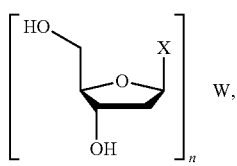

or a solvate, hydrate, polymorph, co-crystal, tautomer, stereoisomer, isotopically labeled derivative, or prodrug thereof.

In certain embodiments, the compound is of the formula:

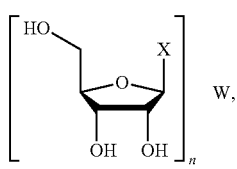

or a solvate, hydrate, polymorph, co-crystal, tautomer, stereoisomer, isotopically labeled derivative, or prodrug thereof.

In certain embodiments, $R^1$ is H. In certain embodiments, $R^1$ is —OH.

In certain embodiments, X is

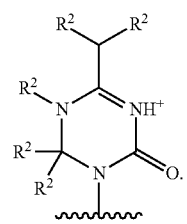

In certain embodiments, X is

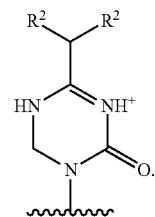

In certain embodiments, X is

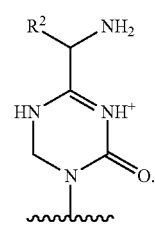

In certain embodiments, X is

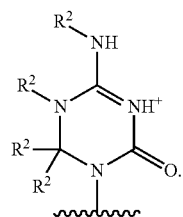

In certain embodiments, X is

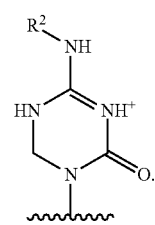

In certain embodiments, X is

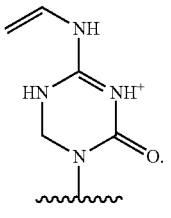 [SMILES: *N1CNC(NC=C)=[NH+]C1=O]

In certain embodiments, X is
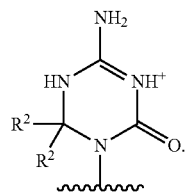
In certain embodiments, X is
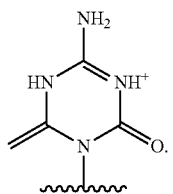 [SMILES: *N1C(=C)NC(N)=[NH+]C1=O]
In certain embodiments, X is
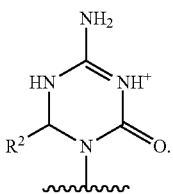
In certain embodiments, X is
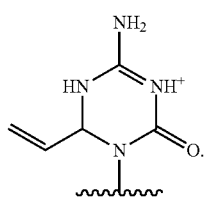 [SMILES: *N1C(=O)[NH+]=C(N)NC1C=C]
In certain embodiments, X is
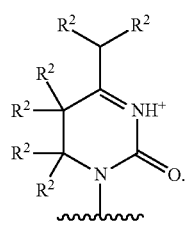
In certain embodiments, X is
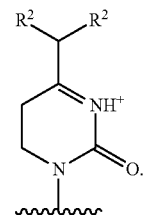
In certain embodiments, X is
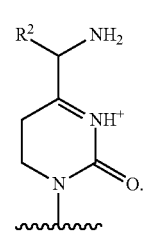
In certain embodiments, X is
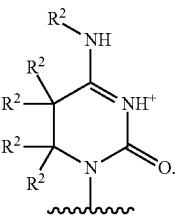
In certain embodiments, X is
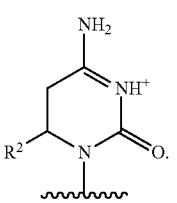
In certain embodiments, X is
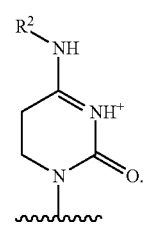

In certain embodiments, X is
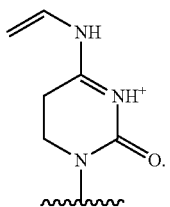 [SMILES: *N1CCC(NC=C)=[NH+]C1=O]
In certain embodiments, X is
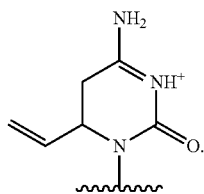 [SMILES: *N1C(=O)[NH+]=C(N)CC1C=C]
In certain embodiments, X is
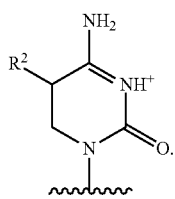
In certain embodiments, X is
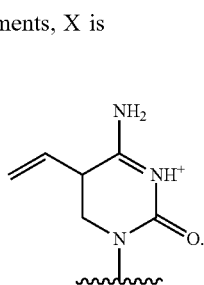
In certain embodiments, X is
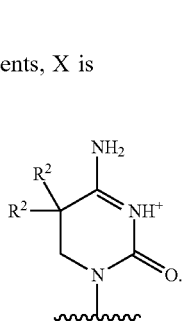
In certain embodiments, X is
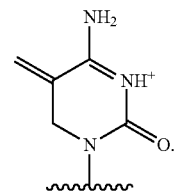 [SMILES: *N1CC(=C)C(N)=[NH+]C1=O]
In certain embodiments, X is
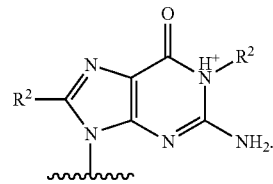
In certain embodiments, X is
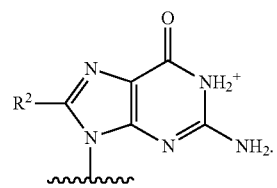
In certain embodiments, X is
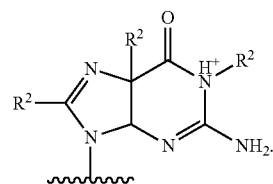
In certain embodiments, X is
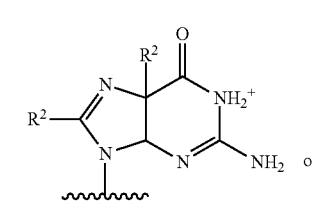 or 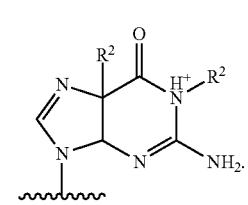

In certain embodiments, X is
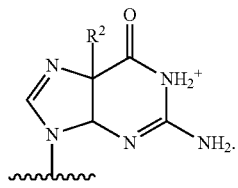
In certain embodiments, X is
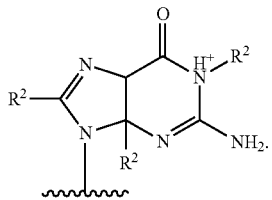
In certain embodiments, X is
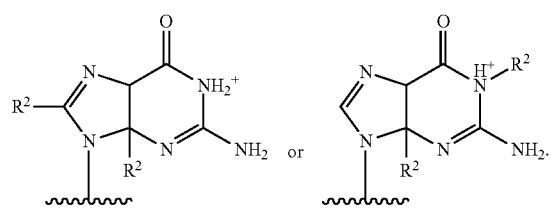
In certain embodiments, X is
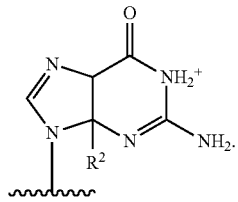
In certain embodiments, X is
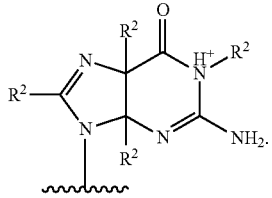
In certain embodiments, X is
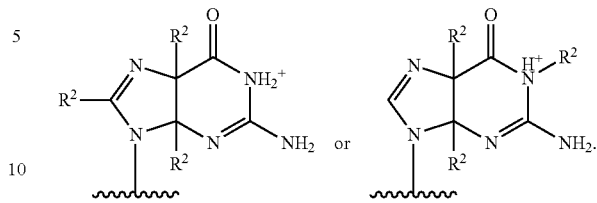
In certain embodiments, X is
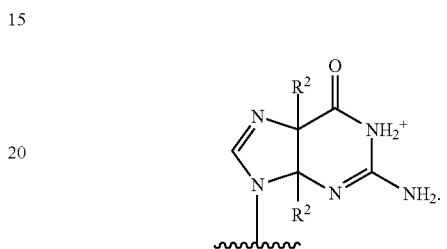
In certain embodiments, X is
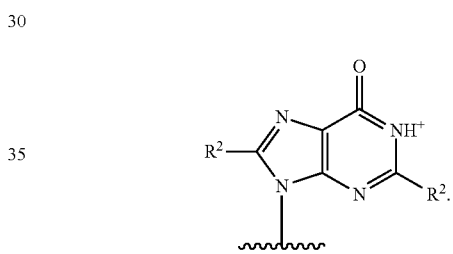
In certain embodiments, X is
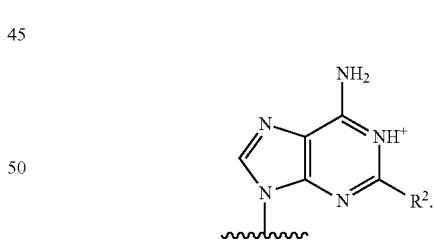
In certain embodiments, X is
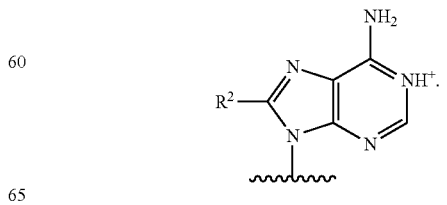

In certain embodiments, X is

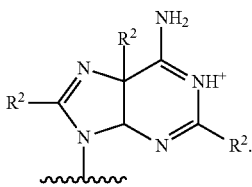

In certain embodiments, X is

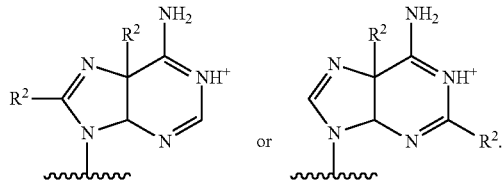

In certain embodiments, X is

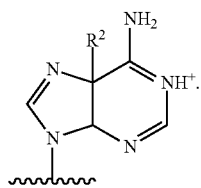

In certain embodiments, X is

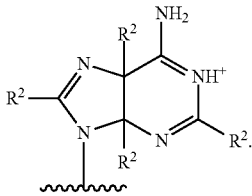

In certain embodiments, X is

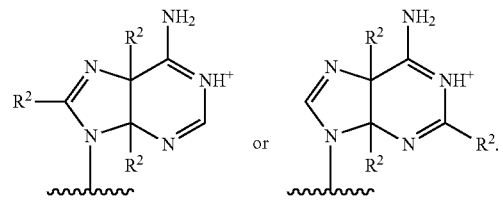

In certain embodiments, X is

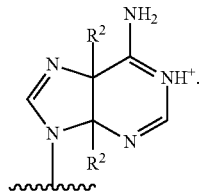

In certain embodiments, Y is —O—.

In certain embodiments, Y is —NR$^2$—, optionally wherein R$^2$ is —C(=O)R$^a$, —C(=O)OR$^a$, —C(=O)N(R$^a$)$_2$, substituted or unsubstituted alkyl, substituted or unsubstituted alkenyl, or substituted or unsubstituted aryl. In certain embodiments, Y is —NH—.

In certain embodiments, Y is —C(R$^2$)$_2$—, optionally wherein each instance of R$^2$ is independently halogen, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$ N(R$^a$)$_2$, —OC(=O)R$^a$, —OC(=O)OR$^a$, —OC(=O)N(R$^a$)$_2$, —SeR$^a$, —N(R$^a$)$_3$$^+$, —O—OR$^a$, —N=NR$^a$, —N$_3$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —NO, —C(=O)-halide, substituted or unsubstituted alkyl, substituted or unsubstituted alkenyl, or substituted or unsubstituted aryl. In certain embodiments, Y is —C(R$^2$)$_2$—, optionally wherein each instance of R$^2$ is independently halogen, —OR$^a$, —N(R$^a$)$_2$, —SR$^a$, —CN, —C(=O)R$^a$, —C(=O)OR$^a$, —NO$_2$, —SeR$^a$, —N(R$^a$)$_3$$^+$, —O—OR$^a$, —N=NR$^a$, —N$_3$, —S(=O)$_2$R$^a$, —S(=O)$_2$OR$^a$, —NO, —C(=O)-halide, substituted or unsubstituted alkyl, substituted or unsubstituted alkenyl, or substituted or unsubstituted aryl. In certain embodiments, Y is —C(R$^2$)$_2$—, wherein the two instances of R$^2$ are joined to form substituted or unsubstituted alkenyl. In certain embodiments, Y is =CH$_2$. In certain embodiments, Y is —C(=O)—.

In certain embodiments, Y is —CHR$^2$—, optionally wherein R$^2$ is halogen, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, —OC(=O)N(R$^a$)$_2$, —SeR$^a$, —N(R$^a$)$_3$$^+$, —O—OR$^a$, —N=NR$^a$, —N$_3$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —NO, —C(=O)-halide, substituted or unsubstituted alkyl, substituted or unsubstituted alkenyl, or substituted or unsubstituted aryl. In certain embodiments, Y is —CHR$^2$—, optionally wherein R$^2$ is halogen, —OR$^a$, —N(R$^a$)$_2$, —SR$^a$, —CN, —C(=O)R$^a$, —C(=O)OR$^a$, —NO$_2$, —SeR$^a$, —N(R$^a$)$_3$$^+$, —O—OR$^a$, —N=NR$^a$, —N$_3$, —S(=O)$_2$R$^a$, —S(=O)$_2$OR$^a$, —NO, —C(=O)-halide, substituted or unsubstituted alkyl, substituted or unsubstituted alkenyl, or substituted or unsubstituted aryl. In certain embodiments, Y is —CH(vinyl)-.

In certain embodiments, Y is —CH$_2$—.

Formula (I) may include one or more instances of substituent R$^a$. When Formula (I) includes two or more instances of $R^a$, any two instances of $R^a$ may be the same or different from each other. In certain embodiments, at least one instance of $R^a$ is H. In certain embodiments, each instance of $R^a$ is H. In certain embodiments, at least one instance of $R^a$ is substituted or unsubstituted alkyl (e.g., substituted or unsubstituted $C_{1-6}$ alkyl). In certain embodiments, at least one instance of $R^a$ is substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl (e.g., substituted or unsubstituted phenyl), substituted or unsubstituted heteroaryl, a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. In certain embodiments, two instances of $R^a$ are joined to form a substituted or unsubstituted, heterocyclic ring, or substituted or unsubstituted, heteroaryl ring.

In certain embodiments, at least one instance of alkyl is unsubstituted alkyl (e.g., unsubstituted $C_{1-6}$ alkyl (e.g., Me, Et, Pr, or Bu)). In certain embodiments, at least one instance of alkyl is substituted alkyl (e.g., substituted $C_{1-6}$ alkyl). In certain embodiments, at least one instance of alkyl is substituted with one or more substituents independently selected from the group consisting of halogen, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$N(R^a)C(=O)R^a$, —$N(R^a)C(=O)OR^a$, —$N(R^a)C(=O)N(R^a)_2$, —$N(R^a)S(=O)R^a$, —$N(R^a)S(=O)OR^a$, —$N(R^a)S(=O)N(R^a)_2$, —$N(R^a)S(=O)_2R^a$, —$N(R^a)S(=O)_2OR^a$, —$N(R^a)S(=O)_2N(R^a)_2$, —$OC(=O)R^a$, —$OC(=O)OR^a$, —$OC(=O)N(R^a)_2$, —$SeR^a$, —$N(R^a)_3^+$, —O—$OR^a$, —N=$NR^a$, —$N_3$, —$S(=O)R^a$, —$S(=O)OR^a$, —$S(=O)N(R^a)_2$, —$S(=O)_2R^a$, —$S(=O)_2OR^a$, —$S(=O)_2N(R^a)_2$, —NO, —C(=O)-halide, substituted or unsubstituted alkyl, substituted or unsubstituted alkenyl, and substituted or unsubstituted aryl. In certain embodiments, at least one instance of alkyl is substituted with one or more substituents independently selected from the group consisting of halogen, —$OR^a$, —$N(R^a)_2$, —$SR^a$, —CN, —$C(=O)R^a$, —$C(=O)OR^a$, —$NO_2$, —$SeR^a$, —$N(R^a)_3^+$, —O—$OR^a$, —N=$NR^a$, —$N_3$, —$S(=O)_2R^a$, —$S(=O)_2OR^a$, —NO, —C(=O)-halide, substituted or unsubstituted alkyl, substituted or unsubstituted alkenyl, or substituted or unsubstituted aryl.

In certain embodiments, at least one instance of alkenyl is unsubstituted alkenyl (e.g., unsubstituted $C_{1-6}$ alkenyl (e.g., =$CH_2$, vinyl, or allyl)). In certain embodiments, at least one instance of alkenyl is substituted alkenyl (e.g., substituted $C_{1-6}$ alkenyl). In certain embodiments, at least one instance of alkenyl is substituted with one or more substituents independently selected from the group consisting of halogen, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$N(R^a)C(=O)R^a$, —$N(R^a)C(=O)OR^a$, —$N(R^a)C(=O)N(R^a)_2$, —$N(R^a)S(=O)R^a$, —$N(R^a)S(=O)OR^a$, —$N(R^a)S(=O)N(R^a)_2$, —$N(R^a)S(=O)_2R^a$, —$N(R^a)S(=O)_2OR^a$, —$N(R^a)S(=O)_2N(R^a)_2$, —$OC(=O)R^a$, —$OC(=O)OR^a$, —$OC(=O)N(R^a)_2$, —$SeR^a$, —$N(R^a)_3^+$, —O—$OR^a$, —N=$NR^a$, —$N_3$, —$S(=O)R^a$, —$S(=O)OR^a$, —$S(=O)N(R^a)_2$, —$S(=O)_2R^a$, —$S(=O)_2OR^a$, —$S(=O)_2N(R^a)_2$, —NO, —C(=O)-halide, substituted or unsubstituted alkyl, substituted or unsubstituted alkenyl, and substituted or unsubstituted aryl. In certain embodiments, at least one instance of alkenyl is substituted with one or more substituents independently selected from the group consisting of halogen, —$OR^a$, —$N(R^a)_2$, —$SR^a$, —CN, —$C(=O)R^a$, —$C(=O)OR^a$, —$NO_2$, —$SeR^a$, —$N(R^a)_3^+$, —O—$OR^a$, —N=$NR^a$, —$N_3$, —$S(=O)_2R^a$, —$S(=O)_2OR^a$, —NO, —C(=O)-halide, substituted or unsubstituted alkyl, substituted or unsubstituted alkenyl, or substituted or unsubstituted aryl.

In certain embodiments, at least one instance of aryl is 6- to 10-membered aryl. In certain embodiments, at least one instance of aryl is unsubstituted aryl (e.g., unsubstituted phenyl). In certain embodiments, at least one instance of aryl is substituted aryl (e.g., substituted phenyl). In certain embodiments, at least one instance of aryl is substituted with one or more substituents independently selected from the group consisting of halogen, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$N(R^a)C(=O)R^a$, —$N(R^a)C(=O)OR^a$, —$N(R^a)C(=O)N(R^a)_2$, —$N(R^a)S(=O)R^a$, —$N(R^a)S(=O)OR^a$, —$N(R^a)S(=O)N(R^a)_2$, —$N(R^a)S(=O)_2R^a$, —$N(R^a)S(=O)_2OR^a$, —$N(R^a)S(=O)_2N(R^a)_2$, —$OC(=O)R^a$, —$OC(=O)OR^a$, —$OC(=O)N(R^a)_2$, —$SeR^a$, —$N(R^a)_3^+$, —O—$OR^a$, —N=$NR^a$, —$N_3$, —$S(=O)R^a$, —$S(=O)OR^a$, —$S(=O)N(R^a)_2$, —$S(=O)_2R^a$, —$S(=O)_2OR^a$, —$S(=O)_2N(R^a)_2$, —NO, —C(=O)-halide, substituted or unsubstituted alkyl, substituted or unsubstituted alkenyl, and substituted or unsubstituted aryl. In certain embodiments, at least one instance of aryl is substituted with one or more substituents independently selected from the group consisting of halogen, —$OR^a$, —$N(R^a)_2$, —$SR^a$, —CN, —$C(=O)R^a$, —$C(=O)OR^a$, —$NO_2$, —$SeR^a$, —$N(R^a)_3^+$, —O—$OR^a$, —N=$NR^a$, —$N_3$, —$S(=O)_2R^a$, —$S(=O)_2OR^a$, —NO, —C(=O)-halide, substituted or unsubstituted alkyl, substituted or unsubstituted alkenyl, or substituted or unsubstituted aryl.

In certain embodiments, U is —O—.

In certain embodiments, U is —$NR^2$—, optionally wherein $R^2$ is —$C(=O)R^a$, —$C(=O)OR^a$, —$C(=O)N(R^a)_2$, substituted or unsubstituted alkyl, substituted or unsubstituted alkenyl, or substituted or unsubstituted aryl. In certain embodiments, U is —NH—.

In certain embodiments, U is —$C(R^2)_2$—, optionally wherein each instance of $R^2$ is independently halogen, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$N(R^a)C(=O)R^a$, —$N(R^a)C(=O)OR^a$, —$N(R^a)C(=O)N(R^a)_2$, —$N(R^a)S(=O)R^a$, —$N(R^a)S(=O)OR^a$, —$N(R^a)S(=O)N(R^a)_2$, —$N(R^a)S(=O)_2R^a$, —$N(R^a)S(=O)_2OR^a$, —$N(R^a)S(=O)_2N(R^a)_2$, —$OC(=O)R^a$, —$OC(=O)OR^a$, —$OC(=O)N(R^a)_2$, —$SeR^a$, —$N(R^a)_3^+$, —O—$OR^a$, —N=$NR^a$, —$N_3$, —$S(=O)R^a$, —$S(=O)OR^a$, —$S(=O)N(R^a)_2$, —$S(=O)_2R^a$, —$S(=O)_2OR^a$, —$S(=O)_2N(R^a)_2$, —NO, —C(=O)-halide, substituted or unsubstituted alkyl, substituted or unsubstituted alkenyl, or substituted or unsubstituted aryl. In certain embodiments, U is —$C(R^2)_2$—, optionally wherein each instance of $R^2$ is independently halogen, —$OR^a$, —$N(R^a)_2$, —$SR^a$, —CN, —$C(=O)R^a$, —$C(=O)OR^a$, —$NO_2$, —$SeR^a$, —$N(R^a)_3^+$, —O—$OR^a$, —N=$NR^a$, —$N_3$, —$S(=O)_2R^a$, —$S(=O)_2OR^a$, —NO, —C(=O)-halide, substituted or unsubstituted alkyl, substituted or unsubstituted alkenyl, or substituted or unsubstituted aryl. In certain embodiments, U is —$C(R^2)_2$—, wherein the two instances of $R^2$ are joined to form substituted or unsubstituted alkenyl. In certain embodiments, U is =CH$_2$. In certain embodiments, U is —C(=O)—.

In certain embodiments, U is —CHR$^2$—, optionally wherein R$^2$ is halogen, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, —OC(=O)N(R$^a$)$_2$, —SeR$^a$, —N(R$^a$)$_3$$^+$, —O—OR$^a$, —N=NR$^a$, —N$_3$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —NO, —C(=O)-halide, substituted or unsubstituted alkyl, substituted or unsubstituted alkenyl, or substituted or unsubstituted aryl. In certain embodiments, U is —CHR$^2$—, optionally wherein R$^2$ is halogen, —OR$^a$, —N(R$^a$)$_2$, —SR$^a$, —CN, —C(=O)R$^a$, —C(=O)OR$^a$, —NO$_2$, —SeR$^a$, —N(R$^a$)$_3$$^+$, —O—OR$^a$, —N=NR$^a$, —N$_3$, —S(=O)$_2$R$^a$, —S(=O)$_2$OR$^a$, —NO, —C(=O)-halide, substituted or unsubstituted alkyl, substituted or unsubstituted alkenyl, or substituted or unsubstituted aryl. In certain embodiments, U is —CH(vinyl)-.

In certain embodiments, U is —CH$_2$—.

In certain embodiments, Z is —O—. In certain embodiments, Z is —S—. In certain embodiments, Z is —NH—.

In certain embodiments, Z is —C(R$^2$)$_2$—, optionally wherein each instance of R$^2$ is independently halogen, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, —OC(=O)N(R$^a$)$_2$, —SeR$^a$, —N(R$^a$)$_3$$^+$, —O—OR$^a$, —N=NR$^a$, —N$_3$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —NO, —C(=O)-halide, substituted or unsubstituted alkyl, substituted or unsubstituted alkenyl, or substituted or unsubstituted aryl. In certain embodiments, Z is —C(R$^2$)$_2$—, optionally wherein each instance of R$^2$ is independently halogen, —OR$^a$, —N(R$^a$)$_2$, —SR$^a$, —CN, —C(=O)R$^a$, —C(=O)OR$^a$, —NO$_2$, —SeR$^a$, —N(R$^a$)$_3$$^+$, —O—OR$^a$, —N=NR$^a$, —N$_3$, —S(=O)$_2$R$^a$, —S(=O)$_2$OR$^a$, —NO, —C(=O)-halide, substituted or unsubstituted alkyl, substituted or unsubstituted alkenyl, or substituted or unsubstituted aryl. In certain embodiments, Z is —C(R$^2$)$_2$—, wherein the two instances of R$^2$ are joined to form substituted or unsubstituted alkenyl. In certain embodiments, Z is =CH$_2$. In certain embodiments, Z is —C(=O)—.

In certain embodiments, Z is —CHR$^2$—, optionally wherein R$^2$ is halogen, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, —OC(=O)N(R$^a$)$_2$, —SeR$^a$, —N(R$^a$)$_3$$^+$, —O—OR$^a$, —N=NR$^a$, —N$_3$, —S(=O)R$^a$, —S(=O)OR$^a$, —S(=O)N(R$^a$)$_2$, —S(=O)$_2$R$^a$, —S(=O)$_2$OR$^a$, —NO, —C(=O)-halide, substituted or unsubstituted alkyl, substituted or unsubstituted alkenyl, or substituted or unsubstituted aryl. In certain embodiments, Z is —CH(vinyl)-.

In certain embodiments, Z is —CH$_2$—.

Formula (I) may include one or more instances of substituent R$^2$. When Formula (I) includes two or more instances of R$^2$, any two instances of R$^2$ may be the same or different from each other. In certain embodiments, at least one instance of R$^2$ is H. In certain embodiments, each instance of R$^2$ is H. In certain embodiments, at least one instance of R$^2$ is an electron-withdrawing group. In certain embodiments, at least one instance of R$^2$ is an electron-donating group. In certain embodiments, each of the electron-withdrawing group and electron-donating group is independently:

if attached to a carbon atom: halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, —OC(=O)N(R$^a$)$_2$, —SeR$^a$, —N(R$^a$)$_3$$^+$, —O—OR$^a$, —N=NR$^a$, —N$_3$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —NO, or —C(=O)-halide, or two instances of R$^2$ on a same carbon atom are joined to form oxo or substituted or unsubstituted alkenyl; or if attached to a nitrogen atom: substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, or a nitrogen protecting group.

In certain embodiments, each of the electron-withdrawing group and electron-donating group is independently: group if attached to a carbon atom: halogen, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, —OC(=O)N(R$^a$)$_2$, —SeR$^a$, —N(R$^a$)$_3$$^+$, —O—OR$^a$, —N=NR$^a$, —N$_3$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —NO, —C(=O)-halide, substituted or unsubstituted alkyl, substituted or unsubstituted alkenyl, or substituted or unsubstituted aryl; or if attached to a nitrogen atom: —C(=O)R$^a$, —C(=O)OR$^a$, —C(=O)N(R$^a$)$_2$, substituted or unsubstituted alkyl, substituted or unsubstituted alkenyl, or substituted or unsubstituted aryl.

In certain embodiments, each of the electron-withdrawing group and electron-donating group, if attached to a carbon atom, is independently halogen, —OR$^a$, —N(R$^a$)$_2$, —SR$^a$, —CN, —C(=O)R$^a$, —C(=O)OR$^a$, —NO$_2$, —SeR$^a$, —N(R$^a$)$_3$$^+$, —O—OR$^a$, —N=NR$^a$, —N$_3$, —S(=O)$_2$R$^a$, —S(=O)$_2$OR$^a$, —NO, —C(=O)-halide, substituted or unsubstituted alkyl, substituted or unsubstituted alkenyl, or substituted or unsubstituted aryl.

In certain embodiments, each of the electron-withdrawing group and electron-donating group, if attached to a carbon atom, is independently F, Cl, or —OH.

In certain embodiments, W is a monovalent anionic counterion. In certain embodiments, W is a bivalent anionic counterion. In certain embodiments, W is a trivalent anionic counterion. In certain embodiments, W is F$^-$, Cl$^-$, Br$^-$, I$^-$, NO$_3^-$, ClO$_4^-$, OH$^-$, H$_2$PO$_4^-$, HPO$_4^{2-}$, PO$_4^{3-}$, HSO$_4^-$, SO$_4^{2-}$, OTf$^-$, OTs$^-$, OMs$^-$, OAc$^-$, OBz$^-$, BF$_4^-$, PF$_4^-$, PF$_6^-$, AsF$_6^-$, or SbF$_6^-$.

In certain embodiments, n is 1. In certain embodiments, n is 2. In certain embodiments, n is 3. In certain embodiments, W and n are such that the compounds described herein are electrically neutral.

In certain embodiments, the pK$_a$ of a compound described herein is between 6 and 8, inclusive. In certain embodiments, the pK$_a$ of a compound described herein is between 6.5 and 7.5, inclusive. In certain embodiments, the pK$_a$ is determined by titration.

V of Formula (II) is as described herein for X of Formula (I), except that the moieties

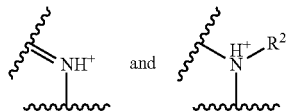

in X is changed to the moieties

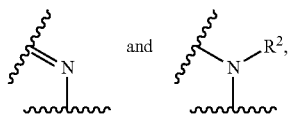

respectively, in V.

R$^1$, Y, U, Z, R$^2$, and any moieties included in R$^1$, Y, U, Z, and/or R$^2$, of Formula (II) are as described herein for Formula (I). The pK$_a$ of a compound of Formula (II) is also as described herein for a compound of Formula (I).

In certain embodiments, the compounds described herein are compounds of Formula (I), and solvates, hydrates, polymorphs, co-crystals, tautomers, stereoisomers, isotopically labeled derivatives, and prodrugs thereof. In certain embodiments, the compounds described herein are compounds of Formula (I), and tautomers and stereoisomers thereof. In certain embodiments, the compounds described herein are compounds of Formula (I), and tautomers thereof. In certain embodiments, the compounds described herein are compounds of Formula (II), and pharmaceutically acceptable salts, solvates, hydrates, polymorphs, co-crystals, tautomers, stereoisomers, isotopically labeled derivatives, and prodrugs thereof. In certain embodiments, the compounds described herein are compounds of Formula (II), and pharmaceutically acceptable salts, tautomers, and stereoisomers thereof. In certain embodiments, the compounds described herein are compounds of Formula (II), and pharmaceutically acceptable salts and tautomers thereof.

The compounds described herein are nucleoside analogs. The compounds are expected to show multiple tautomerism (e.g., enol tautomerism and/or imine tautomerism) and mutagenesis (e.g., against a virus or cancer cell). The compounds may also show syn-anti rotamerism, ionization, and/or anomerization, each of which may also contribute to the mutagenesis. The formation of ionized base pairs has been proposed to account for the mutagenicity of 5-fluro-uracil (Bonnac, L. F., Mansky, L. M. & Patterson, S. E. Structure-activity relationships and design of viral mutagens and application to lethal mutagenesis. J. Med. Chem. 2013 Dec. 12; 56(23):9403-14). The telltale sign of the involvement of ionized base pairs is a pH dependence of mutagenicity. The other mechanism that may contribute to mutagenesis involves the anomerization of the sugar portion of the nucleoside, generating an alpha-anomer (Matoušová, M. et al. 2'-deoxy-5,6-dihydro-5-azacytidine—a less toxic alternative of 2'-deoxy-5-azacytidine: a comparative study of hypomethylating potential. Epigenetics 6, 769-776 (2011)).

Mutagenic nucleoside analogs may act through lethal mutagenesis. Lethal mutagenesis is a strategy whereby the innate immune system or mutagenic pool nucleotides increase the error rate of viral replication above the error catastrophe limit. Lethal mutagenesis can also increase the mutation rate of the DNA and/or RNA of cancer cells (e.g., cancer cells with a mutator phenotype) to over the error catastrophe limit and thus show genotoxicity and/or mitochondrial toxicity against the cancer cells. Lethal mutagenesis is proposed as a mechanism for several anti-viral compounds, including Ribavirin, which is useful for treating RS virus infection (RSV) and KP1212, a dihydro base which causes A to G and G to A mutations in HIV. NMR and infrared spectroscopy results indicate that KP1212 was shown to exist as a broad ensemble of interconverting tautomers, among which enolic forms dominated. The mutagenic properties of KP1212 were determined empirically by in vitro and in vivo replication of a single-stranded vector containing a single KP1212. It was found that KP1212, a cytosine mimic, paired with guanine approximately 90% of the time and paired with adenine about 10% of the time under physiological conditions. KP1212 was found to be mutagenic in vivo, causing about 10% C-to-T mutations when present in a template strand. A model is proposed that correlates the mutagenicity of KP1212 with its tautomeric distribution in solution. When incorporated into HIV DNA by RT, KP1212 allows DNA synthesis to continue. However, the modified base of KP1212 is able to tautomerize and base-pair alternately with guanine and adenine. It has been demonstrated that the mutagenic properties of KP1212 are due to its ability to exist as rapidly interconverting isomers, mainly tautomers, which have promiscuous base-pairing abilities. Variable temperature (VT) nuclear magnetic resonance (NMR) techniques have allowed the identification of compounds capable of multiple tautomerism.

Without wishing to be bound by any particular theory, the hydrogenation of the 5,6-double bond in the pyrimidine motif contributes greatly to the efficacy of KP1212 as a mutagenic nucleoside analog. Hydrogenation breaks the aromaticity of the pyrimidine base moiety, causing the electron density on the ring to become more localized. In addition, the heterocyclic ring may become puckered at the 5- and 6-positions when the aromaticity is broken. This puckering could contribute to the low cytotoxicity of KP1212, as human DNA polymerases may reject KP1212 due to its unnatural puckered shape. Therefore, the compounds described herein are expected to show multiple tautomerism as does KP1212, and thus can mimic the mutagenesis and/or hypomethylation properties of KP1212.

The compounds described herein may be structurally similar to natural nucleosides, and the different tautomeric forms of the compounds may cause different responses by the genome of a virus or cancer cell. Therefore, the mutation rate of the genome (e.g., RNA and/or DNA) of the virus or cancer cell may be increased. For example, the compounds described herein may be taken up by a virus-infected cell or a cancer cell as a nucleoside and be phosphorylated by cellular kinases to the corresponding deoxynucleoside triphosphate(s). These can induce mutagenesis.

Many viruses exhibit a high mutation rate when replicating their genomes, enabling quick adaptation to both changing cellular environments and therapeutics (Frenkel, L. M. et al. Multiple viral genetic analyses detect low-level human immunodeficiency virus type 1 replication during effective highly active antiretroviral therapy. J. Virol. 77, 5721-5730 (2003); Mullins, J. I. & Jensen, M. A. Evolutionary dynamics of HIV-1 and the control of AIDS. Curr. Top. Microbiol. Immunol. 299, 171-192 (2006); Johnston, R. HIV cure: controversy, consensus, and a consortium. AIDS Res. Hum. Retroviruses 26, 943-946 (2010); Esté, J. A. & Cihlar, T. Current status and challenges of antiretroviral research and therapy. Antiviral Res. 85, 25-33 (2010); Broder, S. The development of antiretroviral therapy and its impact on the HIV-1/AIDS pandemic. Antiviral Res. 85, 1-18 (2010)). Mammalian innate immune systems have developed a mechanism to exploit this high mutation rate against the virus; in a phenomenon termed "lethal mutagenesis," (Eigen, M. Error catastrophe and antiviral strategy. Proc. Natl. Acad. Sci. U.S.A. 99, 13374-13376 (2002); Loeb, L. A. et al. Lethal mutagenesis of HIV with mutagenic nucleoside analogs. Proc. Natl. Acad. Sci. U.S.A. 96, 1492-1497 (1999); Smith, R. A., Loeb, L. A. & Preston, B. D. Lethal mutagenesis of HIV. Virus Res. 107, 215-228 (2005); Clouser, C. L., Patterson, S. E. & Mansky, L. M. Exploiting drug repositioning for discovery of a novel HIV combination therapy. J. Virol. 84, 9301-9309 (2010); Graci, J. D. & Cameron, C. E. Therapeutically targeting RNA viruses via lethal mutagenesis. Future Virol. 3, 553-566 (2008); Perales, C., Martín, V. & Domingo, E. Lethal mutagenesis of viruses. Curr. Opin. Virol. 1, 419-422 (2011); Elena, S. F. RNA virus genetic robustness: possible causes and some consequences. Curr. Opin. Virol. 2, 525-530 (2012); De la Torre, J. C. Arenavirus extinction through lethal mutagenesis. Virus Res. 107, 207-214 (2005); Bonnac, L. F., Mansky, L. M. & Patterson, S. E. Structure-activity relationships and design of viral mutagens and application to lethal mutagenesis. J. Med. Chem. (in press) (2013)), the immune system employs nucleic acid-modifying enzymes (e.g., APOBEC and ADAR) to increase the viral mutation rate sharply, stressing the functional gene product repertoire of the virus to the point that the viral population collapses (Koito, A. & Ikeda, T. Intrinsic immunity against retrotransposons by APOBEC cytidine deaminases. Front Microbiol. 4, 28 (2013); Jaszczur, M., Bertram, J. G., Pham, P., Scharff, M. D. & Goodman, M. F. AID and Apobec3G haphazard deamination and mutational diversity. Cell. Mol. Life Sci. 70, 3089-3108 (2013); Smyth, R. P., Davenport, M. P. & Mak, J. The origin of genetic diversity in HIV-1. Virus Res. 169, 415-429 (2012)). Several antiviral agents are proposed to work at least in part by a chemical version of lethal mutagenesis (e.g., ribavirin against hepatitis C virus (Ortega-Prieto, A. M. et al. Extinction of hepatitis C virus by ribavirin in hepatoma cells involves lethal mutagenesis. PLoS ONE 8, e71039 (2013); Dietz, J. et al. Deep sequencing reveals mutagenic effects of ribavirin during monotherapy of hepatitis C virus genotype 1-infected patients. J. Virol. 87, 6172-6181 (2013); Moreno, H., Grande-Pérez, A., Domingo, E. & Martín, V. Arenaviruses and lethal mutagenesis. Prospects for new ribavirin-based interventions. Viruses 4, 2786-2805 (2012); Graci, J. D. & Cameron, C. E. Quasispecies, error catastrophe, and the antiviral activity of ribavirin. Virology 298, 175-180 (2002); Crotty, S. et al. The broad-spectrum antiviral ribonucleoside ribavirin is an RNA virus mutagen. Nat. Med. 6, 1375-1379 (2000)), 5-hydroxy-2'-deoxycytidine against HIV (Loeb, L. A. et al. Lethal mutagenesis of HIV with mutagenic nucleoside analogs. Proc. Natl. Acad. Sci. U.S.A. 96, 1492-1497 (1999)) and T-705 against influenza viruses (Baranovich, T. et al. T-705 (favipiravir) induces lethal mutagenesis in influenza A H1N1 viruses in vitro. J. Virol. 87, 3741-3751 (2013))). When a sufficient number of these mutagenic nucleoside analogs is incorporated into viral genomes, the analogs increase the viral mutation rate above the error catastrophe limit, the rate above which no viable progeny are produced (Eigen, M. Error catastrophe and antiviral strategy. Proc. Natl. Acad. Sci. U.S.A. 99, 13374-13376 (2002); Manrubia, S. C., Domingo, E. & Lázaro, E. Pathways to extinction: beyond the error threshold. Philos. Trans. R. Soc. Lond., B, Biol. Sci. 365, 1943-1952 (2010); Domingo, E., Sheldon, J. & Perales, C. Viral quasispecies evolution. Microbiol. Mol. Biol. Rev. 76, 159-216 (2012); Domingo, E., Grande-Pérez, A. & Martín, V. Future prospects for the treatment of rapidly evolving viral pathogens: insights from evolutionary biology. Expert Opin. Biol. Ther. 8, 1455-1460 (2008); Domingo, E. et al. Viruses as quasispecies: biological implications. Curr. Top. Microbiol. Immunol. 299, 51-82 (2006)).

The mutagenic nucleoside triphosphate(s) then can be incorporated during RNA template-directed synthesis of the minus DNA strand of a virus in a virus-infected cell. Mutagenesis in the virus-infected cell may occur more frequently in the genome of the cells because of the incorporation of a mutagenic analog (e.g., a compound described herein) into an RNA-DNA hybrid. First, reverse transcription occurs in the cytoplasm, whereas repair of cellular DNA is a nuclear process. Second, DNA repair enzymes have evolved to utilize double-stranded DNA that is present in a B-type structure, whereas RNA-DNA hybrids are in an A-type structure. In particular, a methyltransferase may fail to repair efficiently altered substrates when present in the DNA strand of an RNA-DNA hybrid. As a result, altered nucleotide residues in the DNA strand are not excised, and they pair with noncomplementary nucleotides. Upon synthesis of a double-stranded viral DNA intermediate, the mutations are fixed; excision of the altered nucleotide would not obliterate the mutation. In contrast, incorporation of the mutagenic analog into the genome of the virus or cancer cell is subject to removal during DNA repair. After integration of the double-stranded viral DNA containing the mutation into the host genome, transcription results in corresponding base substitutions in the viral RNA. Iteration of this process by viral replication or cancerous proliferation will result in the progressive accumulation of mutations throughout the genome; some of these mutations would diminish the replication or proliferation. Eventually the mutations would exceed the error threshold for maintenance of the quasispecies, resulting in a precipitous decline in replication or proliferation.

An advantage of the strategy of lethal mutagenesis is that it circumvents the ability of quickly mutating viruses and cancer cells to adapt and evolve resistance to a specific therapeutic. Additionally, the progressive weakening of the viral stock induced by lethal mutagens also affects the latent pool of integrated viruses (such as HIV), which offers a unique opportunity for achieving, in the case of retroviruses, not only a remission but also a clinical cure.

The present disclosure provides a rational strategy to tune the mutagenicity of nucleoside analogs, leading to the discovery of next-generation lethal mutagens with improved clinical efficacy. For example, it has been shown that KP1212 is only 10% mutagenic, which is 5-fold lower than the theoretical optimum of 50%. The present disclosure describes a strategy to increase the mutagenicity of mutagenicity of nucleoside analogs, such as KP1212. In certain embodiments, the mutagenicity of a nucleoside analog described herein is at least 10%, at least 20%, at least 30%, at least 40%, or at least 45%. In certain embodiments, the mutagenicity of a nucleoside analog described herein is not more than 15%, not more than 20%, not more than 30%, not more than 40%, or not more than 50%.

Figure 1A:
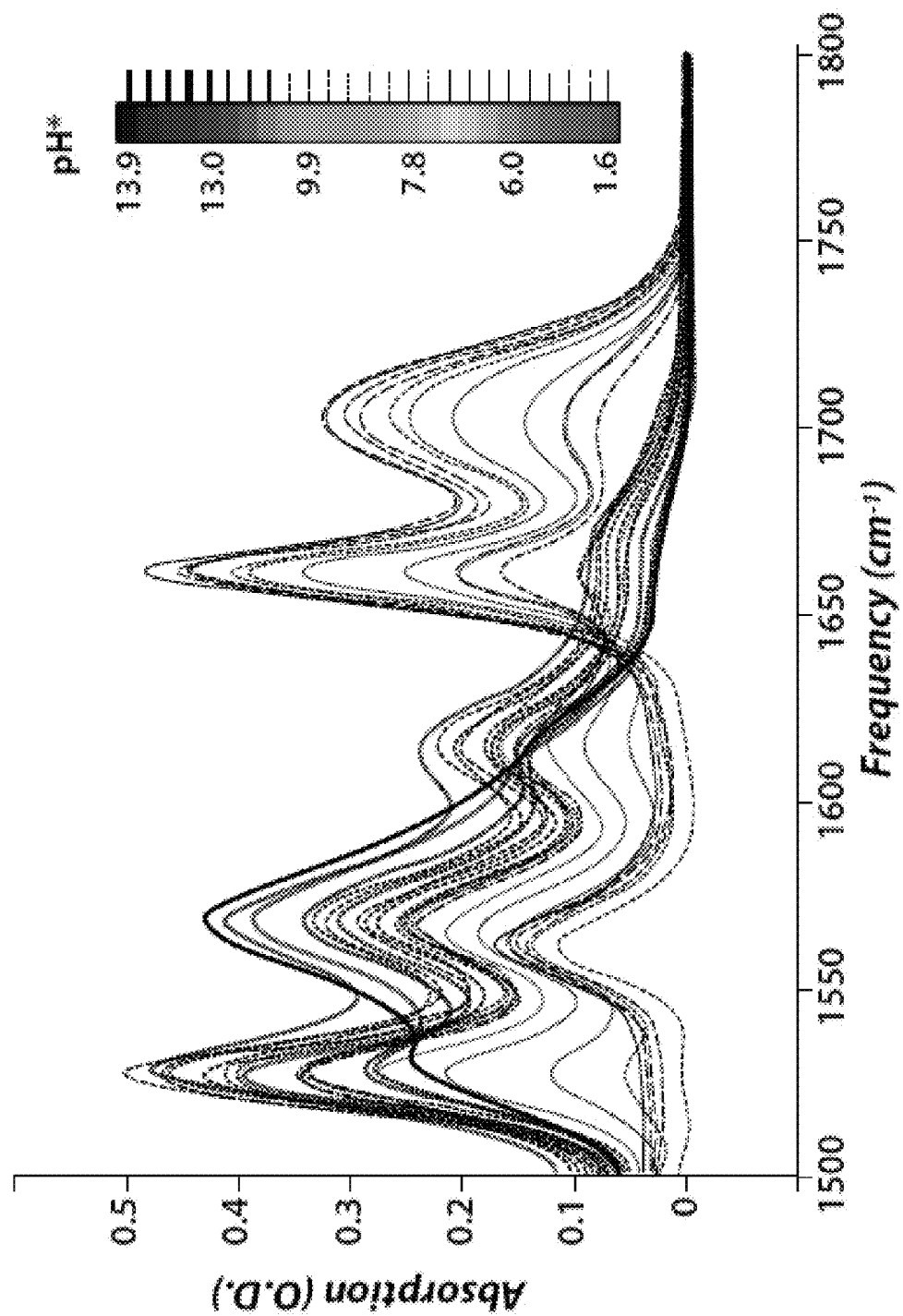
FIGS. 1A to 1E.
Figure 1B:
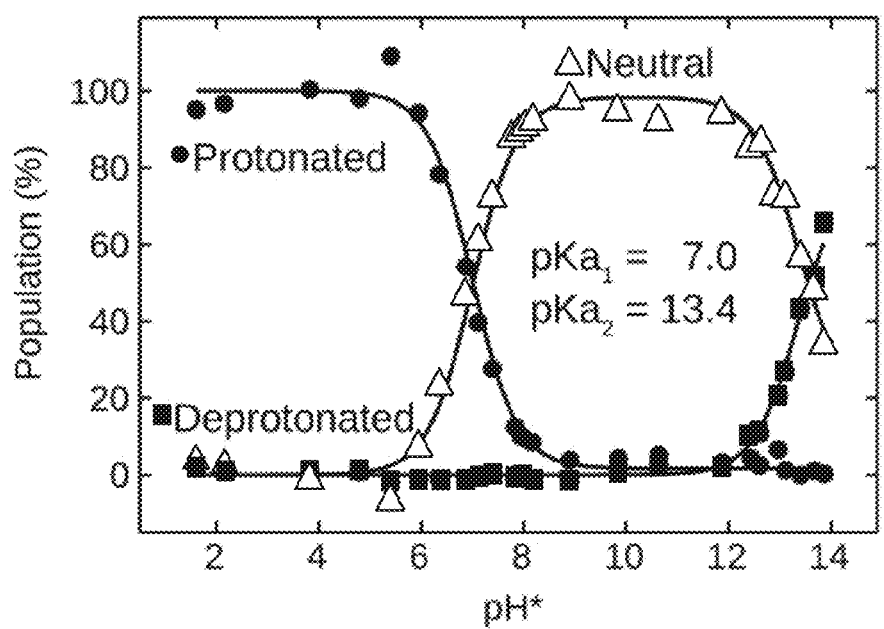
Figure 1C:
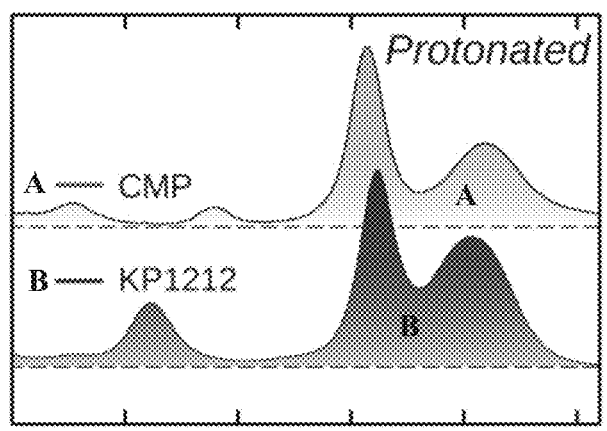
Figure 1D:
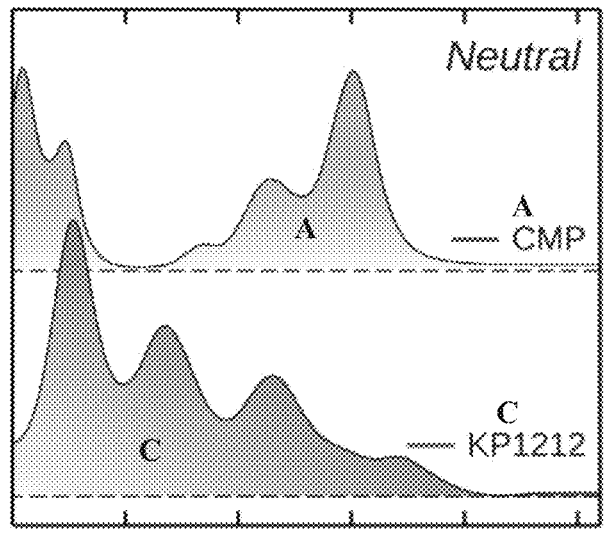
Figure 1E:
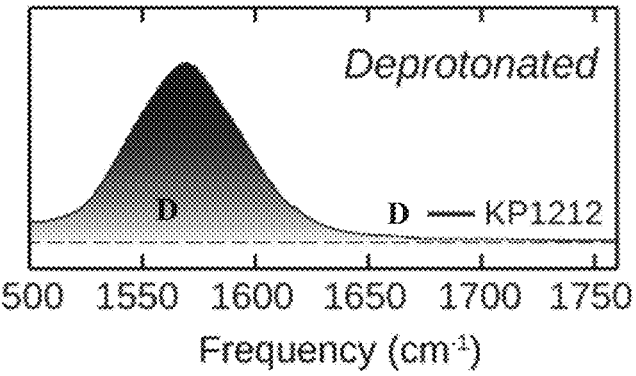
Figure 2:
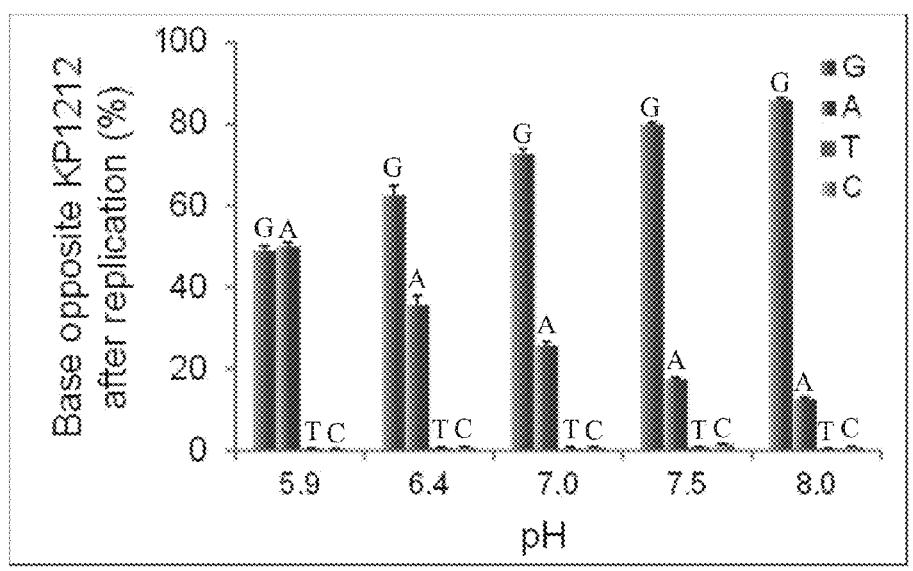
FIG. 2 is a bar graph showing that the mutagenesis of KP1212 depends on pH.

Using 1-dimensional (1D) and/or 2-dimentional (2D) infrared (IR) spectroscopy, it has been showed that KP1212 has a $pK_a$ of about 7 (FIGS. 1A to 1E), a value unusually high when compared with its closest structural analog among the normal bases, dC (show below), which has a $pK_a$ of about 4.3. This finding indicated that, under biologically relevant conditions (e.g., pH being between 6 and 8, inclusive (pH 6-8)), KP1212 exists as a mixture of protonated and unprotonated forms, in addition to the multiple tautomeric forms that were shown to exist previously using low temperature NMR. An in vitro assay has been developed that allowed the measurement of the mutation type and rate of KP1212 at different pH values, and the mutagenic properties of KP1212 have been evaluated at pH 6-8. It has been found that mutagenesis increased as the pH dropped, from about 10% at pH 8 to about 50% at pH 5.9 (FIG. 2). These results suggest that KP1212 in its protonated form is significantly more mutagenic that in the neutral form. By simply changing the pH of a composition (e.g., a bodily fluid or aqueous solution) containing KP1212 to 5.9, KP1212 achieves its optimal mutagenicity of about 50%.

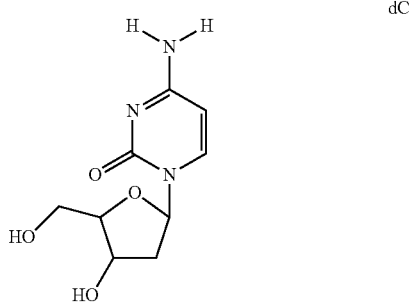 [SMILES: Nc1ccn(C2CC(O)C(CO)O2)c(=O)n1]

dC

The discovery of the pH-dependent mutagenesis of KP1212 suggests that the mutagenicity of a nucleoside analog can be adjusted (or tuned) by varying the pH of a composition (e.g., a bodily fluid or an aqueous solution) that contains the nucleoside analog. If the pH is held constant (e.g., the pH inside the cell under physiological conditions), then the mutagenicity of a nucleoside analog can be adjusted by varying its $pK_a$. The $pK_a$ of a nucleoside analog depends on the electron density of the nucleoside analog. Therefore, by substituting the nucleoside analogs (e.g., substituting the nucleobase moiety of the nucleoside analogs) with electron donating groups and/or electron withdrawing groups, the $pK_a$ of the nucleoside analogs can be adjusted as desired. Examples of such modifications are shown in FIG. 3.

Fine-tuning the mutagenic capabilities of nucleoside analogs by adjusting their $pK_a$ is useful in developing novel lethal mutagens for treating viral infections and cancer.

In addition, the present disclosure provides research tools that are useful in characterizing and evaluating lethal mutagens. For example, provided herein is a method based on matrix algebra that allows deconvolution of NMR spectrum to calculate distribution of tautomeric forms of a nucleoside analog (FIGS. 4A to 4D).

The present disclosure also provides methods based on binding isotope effects to determining tautomeric forms of compounds, optionally in the context of nucleic acids or nucleic acid-protein complexes (FIGS. 5A and 5B). This method is useful in determining tautomeric forms of compounds, e.g., compounds that are preferred by viral and cancer cell polymerases, which will facilitate the development of more targeted mutagens.

Compounds described herein also can be used as hypomethylating agents that inhibit the activity of DNA methyltransferases thereby reducing the methylation and silencing of one or more genes (e.g., tumor suppressors) associated with cancer. Based upon the mechanism of action of 5-methylcytosine forming methyltransferases, which are believed to be epigenome modifying agents, the compounds described herein may be refractory to natural genome methylation. Hence, the compounds described herein may find uses as epigenome modifying agents. Such agents may be useful as analytical reagents to people studying genome regulation. The compounds described herein may also have clinical utility. For example, aberrant DNA methylation and a consequent silencing of cancer-related genes are commonly found in human tumor cells (Matoušová et al., *Epigenetics* 2011, 6, 769-776). Inhibitors of DNA methyltransferases may represent a gentle therapeutic alternative to standard chemotherapy. They are incorporated into the DNA, reactivate methylated genes and protect them from re-methylation. Accordingly, the compounds described herein are useful in treating cancer. In some embodiments, compounds that show multiple tautomerism do not exhibit significant cytotoxicity and can be used therapeutically as hypomethylating agents.

Pharmaceutical Compositions, Kits, and Administration

In another aspect, the present disclosure provides pharmaceutical compositions comprising a compound described herein and optionally a pharmaceutically acceptable excipient, the pharmaceutical compositions are useful in increasing the mutagenicity of a first compound, determining tautomeric forms of a compound, treating a viral infection in a subject in need thereof, increase the mutation rate of a RNA or DNA of a virus, killing a virus, inhibiting the replication of a virus, treating cancer in a subject in need thereof, increasing the mutation rate of a RNA and/or DNA of a cancer cell, inducing apoptosis of a cancer cell, and/or decreasing DNA methylation in a cancer cell.

In certain embodiments, the compound described herein is provided in an effective amount in the pharmaceutical composition. In certain embodiments, the effective amount is a therapeutically effective amount. In certain embodiments, the effective amount is a prophylactically effective amount.

In certain embodiments, the effective amount is an amount effective for killing viruses or cancer cells, inhibiting the replication of viruses, and/or inducing apoptosis in cancel cells, by at least 10%, at least 20%, at least 30%, at least 40%, at least 50%, at least 60%, at least 70%, at least 80%, at least 90%, at least 95%, or at least 98%. In certain embodiments, the effective amount is an amount effective for killing viruses or cancer cells, inhibiting the replication of viruses, and/or inducing apoptosis in cancel cells, by not more than 10%, not more than 20%, not more than 30%, not more than 40%, not more than 50%, not more than 60%, not more than 70%, not more than 80%, not more than 90%, not more than 95%, or not more than 98%.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste); gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the viral infection or cancer being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., potency and/or efficacy), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, antiviral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an antiviral agent. In certain embodiments, the additional pharmaceutical agent is (−)-Oseltamivir, β-D-Ribofuranose, 1-acetate 2,3,5-tribenzoate, 1-Docosanol, 2-Amino-6-chloropurine, 5-Iodo-2'-deoxyuridine, 6-Chloropurine, Abacavir sulfate, Abacavir-epivir mixt., Acyclovir, Acyclovir sodium, Adefovir dipivoxil, Amantadine (e.g. Amantadine hydrochloride), Amantadine hydrochloride, Anti-HIV agent (e.g. Abacavir, Amprenavir, Atazanavir, Azidothymidine, Bryostatin (e.g. Bryostatin 1, Bryostatin 10, Bryostatin 11, Bryostatin 12, Bryostatin 13, Bryostatin 14, Bryostatin 15, Bryostatin 16, Bryostatin 17, Bryostatin 18, Bryostatin 19, Bryostatin 2, Bryostatin 20, Bryostatin 3, Bryostatin 4, Bryostatin 5, Bryostatin 6, Bryostatin 7, Bryostatin 8, Bryostatin 9), Dideoxycytidine, Dideoxyinosine, Efavirenz, Indinavir, Lamivudine, Lopinavir, Nevirapine, Ritonavir, Saquinavir, Stavudine, Tenofovir), Azauridine, ombivir, Deoxynojirimycin, Docosanol, Fomivirsen sodium, Foscarnet, Ganciclovir, Integrase inhibitors (e.g. 5CITEP, Chloropeptin I, Complestatin, Dolutegravir, Elvitegravir, L 708906, L 731988, MK 2048, Raltegravir, Raltegravir potassium), MK 5172, MK 8742, Palivizumab, Pegylated interferon alfa-2b, Phosphonoacetic acid, Ribavirin, Simeprevir, Sofosbuvir, Tubercidin, Vidarabine, Virus entry inhibitor (e.g. Enfuvirtide, Maraviroc), or a combination thereof. In certain embodiments, the additional pharmaceutical agent is anticancer agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRU- VICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPDX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful in increasing the mutagenicity of a first compound, determining tautomeric forms of a compound, treating a viral infection in a subject in need thereof, increase the mutation rate of a RNA or DNA of a virus, killing a virus, inhibiting the replication of a virus, treating cancer in a subject in need thereof, increasing the mutation rate of a RNA and/or DNA of a cancer cell, inducing apoptosis of a cancer cell, and/or decreasing DNA methylation in a cancer cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for increasing the mutagenicity of a first compound, determining tautomeric forms of a compound, treating a viral infection in a subject in need thereof, increase the mutation rate of a RNA or DNA of a virus, killing a virus, inhibiting the replication of a virus, treating cancer in a subject in need thereof, increasing the mutation rate of a RNA and/or DNA of a cancer cell, inducing apoptosis of a cancer cell, and/or decreasing DNA methylation in a cancer cell. A kit described herein may include one or more additional pharmaceutical agents described herein as a separate composition.

Methods of Treatment and Uses

In another aspect, the present disclosure provides methods of increasing the mutagenicity of a first compound, the methods comprising substituting the first compound with one or more electron donating groups and/or electron withdrawing groups to provide a second compound, wherein:
  the first compound is a nucleobase, nucleoside, nucleotide, or an analog thereof; and
    if the $pK_a$ of the first compound is higher than 7, then the $pK_a$ of the second compound is lower than the $pK_a$ of the first compound; or
    if the $pK_a$ of the first compound is lower than 7, then the $pK_a$ of the second compound is higher than the $pK_a$ of the first compound;
    wherein each $pK_a$ is independently a $pK_a$ at 25° C.

In certain embodiments, the $pK_a$ of the second compound is between 5.5 and 8.5, inclusive. In certain embodiments, the $pK_a$ of the second compound is between 6 and 8, inclusive. In certain embodiments, the $pK_a$ of the second compound is between 6.5 and 7.5, inclusive.

In another aspect, the present disclosure provides methods of determining tautomeric forms of a compound, the methods comprising:
  providing the compound in physiological conditions;
  performing a variable temperature 1-dimensional infrared spectroscopy test or a variable temperature 2-dimensional infrared spectroscopy test on the compound; and
  performing a density functional theory calculation on the compound;
  wherein the compound is a nucleobase, nucleoside, nucleotide, or an analog thereof.

In certain embodiments, in the step of providing the compound, the compound is provided in the absence of a polymer (e.g., nucleic acid). In certain embodiments, in the step of providing the compound, the compound is provided further in the presence of a polymer (e.g., nucleic acid). In certain embodiments, in the step of providing the compound, the compound is not part of a polymer (e.g., nucleic acid). In certain embodiments, in the step of providing the compound, the compound is part of a polymer (e.g., nucleic acid). In certain embodiments, the 1-dimensional infrared spectroscopy test is a 1-dimensional Fourier transform infrared spectroscopy test. In certain embodiments, the 2-dimensional infrared spectroscopy test is a 2-dimensional Fourier transform infrared spectroscopy test.

In another aspect, the present disclosure provides methods of determining tautomeric forms of a compound, the methods comprising:
  providing the compound in physiological conditions; and
  performing a density functional theory calculation on the compound to determine the binding isotope effect for each of the tautomeric forms;
  wherein the compound is a nucleobase, nucleoside, nucleotide, or an analog thereof, and interacts non-covalently with a nucleic acid, aptamer, or protein.

In certain embodiments, a method of determining tautomeric forms of a compound further comprises detecting the presence of tautomeric forms (e.g., the presence of a specific tautomeric form) of the compound. In certain embodiments, a method of determining tautomeric forms of a compound further comprises quantitating the relative amount of tautomeric forms (e.g., the relative amount of different tautomeric forms) of the compound.

In certain embodiments, the physiological conditions are aqueous physiological conditions.

In another aspect, the present disclosure provides methods of evaluating the mutagenicity of a compound in different pH conditions, the methods comprising:
  a primer extension reaction on a template strand comprising at a defined site a compound to provide a synthesized strand, wherein the primer extension reaction is performed in a solution buffered at pH between 5.0 and 9.0, inclusive, using a recombinant polymerase and a custom designed primer;
  specifically polymerase chain reaction (PCR) amplifying the synthesized strand to provide a PCR product; and
  analyzing the PCR product using a restriction endonuclease and postlabeling (REAP) assay to quantitate the mutagenicity of the compound present in the template strand;
  wherein the compound is a nucleobase, nucleoside, nucleotide, or an analog thereof.

The method of evaluating the mutagenicity of a compound allows for analyzing the product of a primer extension reaction (by itself a trivial reaction, even if run at different pHs) with the REAP method (this method was published in Delaney, J. C. & Essigmann, J. M., *Methods Enzymol.* 408, 1-15 (2006)). The methods involve a custom primer, of the form 5'-B-A-3' and the following protocol. The A sequence is the actual primer for the extension reaction, and by itself has a low (about 37° C.) melting temperature. The B sequence is unique, and does not anneal anywhere on the M13 template. Its melting temperature is high, at about 70° C. The template of the primer extension reaction is an M13 genome containing at a specific site a modified base (or nucleoside analog). After the primer extension reaction, a PCR reaction is run using two primers; primer 1 is the forward primer used in the REAP method (or a primer annealing on the M13 genome upstream of the lesion site); primer 2 is exactly the sequence B. This method guarantees that only the primer extension product will be PCR amplified, and amplification will not depend on the yield of the primer extension reaction. Therefore, this method allows to detect and analyze mutagenic consequences (including rare events) of nucleoside analogs in a variety of conditions, where the type of polymerase, pH, ionic strength, salt concentration, and inhibitors can be varied over a large range of possibilities.

In certain embodiments, when a compound is a nucleobase, nucleoside, nucleotide, or an analog thereof, the compound is a compound described herein (e.g., a compound of Formula (I) or (II)).

In another aspect, the present disclosure provides methods of treating a viral infection in a subject in need thereof, the methods comprising administering to the subject an effective amount (e.g., therapeutically effective amount) of a compound or pharmaceutical composition described herein.

In another aspect, the present disclosure provides methods of preventing a viral infection in a subject in need thereof, the methods comprising administering to the subject an effective amount (e.g., prophylactically effective amount) of a compound or pharmaceutical composition described herein.

In certain embodiments, the viral infection is an RNA virus infection. In certain embodiments, the viral infection is a retrovirus infection. In certain embodiments, the viral infection is a DNA virus infection. In certain embodiments, the viral infection is Dengue fever, Dengue hemorrhagic fever (DHF), Dengue shock syndrome (DSS), hepatitis A, hepatitis B, hepatitis C, hepatitis D, hepatitis E, hepatitis F, Coxsackie A virus infection, Coxsackie B virus infection, fulminant viral hepatitis, severe acute respiratory syndrome (SARS), viral myocarditis, influenza virus infection (e.g., influenza A virus infection (e.g., an H1N1, H1N2, H2N1, H2N2, H2N3, H3N1, H3N2, H3N8, H5N1, H7N7, H1N2, H9N2, H7N2, H7N3, H7N9, H5N2, H10N7 virus infection), influenza B virus infection, influenza C virus infection), parainfluenza virus infection, an RS virus (RSV) infection (e.g., RSV bronchiolitis, RSV pneumonia, especially an infant and childhood RSV infection and RSV pneumonia in the patients with cardiopulmonary disorders), measles virus infection, vesicular stomatitis virus infection, rabies virus infection, Ebola virus infection, Japanese encephalitis, Junin virus infection, human cytomegalovirus infection, herpes virus infection (e.g., iltovirus infection, mardivirus infection, simplexvirus infection (herpes simplex virus 1 infection), varicellovirus infection, cytomegalovirus infection, muromegalovirus infection, proboscivirus infection, roseolovirus infection, lymphocryptovirus infection, macavirus infection, percavirus infection, rhadinovirus infection), poliovirus infection, Marburg virus infection, Lassa fever virus infection, Venezuelan equine encephalitis, Rift Valley Fever virus infection, Korean hemorrhagic fever virus infection, Crimean-Congo hemorrhagic fever virus infection, HIV infection, acquired immunodeficiency syndrome (AIDS), encephalitis, Saint Louise encephalitis, Kyasanur Forest disease, Murray Valley encephalitis, tick-borne encephalitis, West Nile encephalitis, yellow fever, or a viral infection in subjects with immune disorders. In certain embodiments, the viral infection is an influenza virus infection. In certain embodiments, the viral infection is an influenza A virus infection. In certain embodiments, the viral infection is human flu (e.g., H1N1, H2N2, H3N2, H5N1, H7N7, H1N2, H9N2, H7N2, H7N3, or H10N7 virus infection). In certain embodiments, the viral infection is bird flu (e.g., H5N1 or H7N9 virus infection). In certain embodiments, the viral infection is swine influenza (e.g., H1N1, H1N2, H2N1, H3N1, H3N2, or H2N3 virus infection, or influenza C virus infection). In certain embodiments, the viral infection is equine influenza (e.g., H7N7 or H3N8 virus infection). In certain embodiments, the viral infection is canine influenza (e.g., H3N8 virus infection). In certain embodiments, the viral infection is an influenza B virus infection. In certain embodiments, the viral infection is an influenza C virus infection. In certain embodiments, the viral infection is HIV infection or AIDS. In certain embodiments, the viral infection is hepatitis (e.g., hepatitis B or hepatitis C).

In another aspect, the present disclosure provides methods of increase the mutation rate of a RNA or DNA of a virus, the methods comprising contacting the virus with an effective amount of a compound or pharmaceutical composition described herein.

In another aspect, the present disclosure provides methods of killing a virus, the methods comprising contacting the virus with an effective amount of a compound or pharmaceutical composition described herein.

In another aspect, the present disclosure provides methods of inhibiting the replication of a virus, the methods comprising contacting the virus with an effective amount of a compound or pharmaceutical composition described herein.

In certain embodiments, the virus is a virus causing a viral infection described herein. In certain embodiments, the virus is a RNA virus. In certain embodiments, the virus is a retrovirus. In certain embodiments, the virus is a DNA virus. In certain embodiments, the virus is influenza virus, human immunodeficiency virus (HIV), or hepatitis virus (e.g., hepatitis B virus or hepatitis C virus).

In certain embodiments, the virus is in vitro. In certain embodiments, the virus is in vivo.

In another aspect, the present disclosure provides methods of treating cancer in a subject in need thereof, the methods comprising administering to the subject an effective amount (e.g., therapeutically effective amount) of a compound or pharmaceutical composition described herein.

In certain embodiments, the cancer is acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); a hematopoietic cancer (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; or vulvar cancer (e.g., Paget's disease of the vulva). In certain embodiments, the cancer is a cancer with a mutator phenotype (e.g., a cancer with an increased mutation rate in the cancer cells, compared to a different cancer).

In another aspect, the present disclosure provides methods of increasing the mutation rate of a RNA and/or DNA of a cancer cell, the methods comprising contacting the cancer cell with an effective amount of a compound or pharmaceutical composition described herein.

In another aspect, the present disclosure provides methods of inducing apoptosis of a cancer cell, the methods comprising contacting the cancer cell with an effective amount of a compound or pharmaceutical composition described herein.

In another aspect, the present disclosure provides methods of decreasing DNA methylation in a cancer cell in a subject in need thereof, the methods comprising administering to the subject an effective amount of a compound or pharmaceutical composition described herein.

In certain embodiments, the cancer cell is in vitro. In certain embodiments, the cancer cell is in vivo. In certain embodiments, the cancer cell is a cancer cell with a mutator phenotype.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Preparation of the Compounds Described Herein

The compounds provided herein can be prepared from readily available starting materials using methods known in the art. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures. Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein. For example, the compounds described herein can be prepared according to methods known in the art. See, e.g., Green et al., *Journal of Biological Chemistry* 1957, 228, 601-9. In certain embodiments, the compounds described herein are prepared by hydrogenation using flow chemistry (e.g., hydrogenation catalyzed by rhodium on alumina (Cohn, W. E. and Doherty, D. G. *JACS* 1956, 78, 2863-2868; Green, M. and Cohen, S. S. *J. Biol. Chem.* 1957, 228, 601-609; Hanze, A. R. *JACS* 1967, 89, 6720-6725).

Example 1. IR Spectroscopy Tests of KP1212 in Aqueous Solutions

Methods.

For both 1D FTIR and 2D IR experiments, the H/D exchanged KP1212 was dissolved at a concentration of 20 mg/ml (88 mM) in 0.5 M phosphate buffer pD (pH reading in $D_2O$) 7.9. About 25 μl of sample solution was sandwiched between two $CaF_2$ windows separated by a 50 μm TEFLON spacer. Variable-temperature FTIR spectra were collected using Nicolet 380 FTIR spectrometer at 1.0 $cm^{-1}$ resolution with 16 scans per spectrum. The pH of the sample solution was varied (e.g., from 1.6 to 13.9, e.g., at 1.6 and 7.4, at 25° C.). Spectra for both the sample and the $D_2O$ were collected with the same procedure and the solvent spectra were subtracted from the sample spectra.

Absorptive 2D IR spectra were collected using a 2D IR spectrometer as described in detail previously (Chung, H. S., Khalil, M., Smith, A. W. & Tokmakoff, A. Transient two-dimensional IR spectrometer for probing nanosecond temperature-jump kinetics. *Rev. Sci. Instrum.* 78, 063101 (2007)). The relative polarizations of the pulses were set to be perpendicular (ZZYY). The waiting time (τ2) between the first two pulses and the third pulse was fixed at 150 fs. The coherence time between the first and the second pulse was scanned in 4 fs steps from −60 fs to 2.8 ps and 2.0 ps for rephasing and non-rephasing spectra, respectively. The coherence time (τ1) was Fourier-transformed to obtain the first frequency axis ω1. The heterodyned signal was dispersed in a monochromator to obtain the ω3 frequency dimension and collected using a 64×2 pixel mercury-cadmium-telluride (MCT) array detector. Linear absorption from the solvent and solute was divided out along both the ω1 and ω3 axes to remove spectral distortions (Jones, K. C., Ganim, Z., Peng, C. S. & Tokmakoff, A. Transient two-dimensional spectroscopy with linear absorption corrections applied to temperature-jump two-dimensional infrared. *J. Opt. Soc. Am. B* 29, 118-129 (2012)).

To provide further evidence of the existence of multiple tautomers, 2D IR spectra of KP1212 were recorded. 2D IR spectroscopy is analogous to 2D NMR: sequences of ultra-fast IR pulses are employed to excite molecular vibrations, and the energy flow from one vibration to others is then detected. The correlation of excitation and detection frequencies allows mixtures of tautomers to be separated through the cross-peaks that encode their intramolecular vibrational couplings (Peng, C. S. & Tokmakoff, A. Identification of lactamlactim tautomers of aromatic heterocycles in aqueous solution using 2D IR spectroscopy. *J. Phys. Chem. Lett.* 3, 3302-3306 (2012); Peng, C. S., Baiz, C. R. & Tokmakoff, A. Direct observation of ground-state lactam-lactim tautomerization using temperature-jump transient 2D IR spectroscopy. *Proc. Natl. Acad. Sci. U.S.A.* 110, 9243-9248 (2013)).

Exemplary results are shown in FIGS. 1A to 1E.

Example 2. Mutagenesis of KP1212 Depends on pH

The M13 single-stranded genomes, containing one KP1212 base at a specific site were constructed and purified as previously reported (Li, Fedeles, Singh, Peng et al, 2014, Tautomerism provides a molecular explanation for the mutagenic properties of the anti-HIV nucleoside 5-aza-5,6-dihydro-2'-deoxycytidine, *Proc. Natl. Acad. Sci. U.S.A.* 111, E3252-3259).

Primer extension reactions at various pHs were carried out as follows: 100 fmol extension primer (5'-CGTGAT-CATGCGCAGACTGACATCATGTGTAAAACGACG-GCC AGTGAATTGGA-3') were annealed to 100 fmol M13 genome by heating the mixture at 80° C. for 5 min followed by a slow (0.1° C./s) cooling to 4° C. The primer was extended by 2.5 U of a suitable polymerase (for example Klenow) in a solution containing 50 mM phosphate buffer (pH adjusted from 5.5-8.5 in 0.5 increments), 100 mM $K^+$ (adjusted with KCl), 10 mM $Mg^{2+}$, 1 mM DTT and 125 μM of each of the four dNTPs for 4 h at 30° C. The resulting product was purified using QIAQUICK columns (Qiagen) and then PCR amplified with PFUTURBO polymerase (Agilent) with the primers: 5'-YCAGCTATGACCATGAT-TCAGTGGAAGAC-3' (forward) and 5'-YCGTGATCAT-GCGCAGACTGACATCATGTG-3' (reverse), where Y is a phospho-hexylamino linker which prevents 5' phosphorylation during subsequent steps. Amplification was done in 32 cycles of 95/68/72° C. for 30/30/60 s respectively. The choice of the extension and PCR primers allows for a specific amplification of the newly synthesized strand.

The PCR products were subsequently purified and analyzed with the REAP assay as previously described (Li, Fedeles, Singh, Peng et al, 2014, Tautomerism provides a molecular explanation for the mutagenic properties of the anti-HIV nucleoside 5-aza-5,6-dihydro-2'-deoxycytidine. *Proc. Natl. Acad. Sci. U.S.A.* 111, E3252-3259). The REAP assay results provided the identity (C, T, G, or A) and the relative amount of the base present at the site where KP1212 was initially. Because KP1212 is a cytosine analog, any non-C base is considered a mutagenic outcome. In this example, KP1212 causes more C-to-T mutations as the pH decreases.

Exemplary results are shown in FIG. 2.

Example 3. Binding Isotope Effect (BIE) for Determining the Tautomeric Forms of a Ligand (OxyTPP) Bound to its Target Macromolecule (TPP Riboswitch)

Experimental Method for Using BIEs to Determine Tautomeric Form of OxyTPP Bound to the TPP Riboswitch.

The spectroscopic approaches described above allowed the full characterization of the tautomeric forms of nucleic acid base, nucleoside, nucleotide, and their analogs in the unbound form. Given the complexity of the nucleic acid polymers aptamer, these approaches could not be directly applied to determine the tautomeric form of OxyTPP bound to the riboswitch. To establish the tautomeric form of the bound OxyTPP, experimental binding isotope effects (BIEs) were used, which characterize the increase or decrease in binding upon substitution of an atom with its heavier isotope. BIEs are useful as they are sensitive to change in bond order between two equilibrium states and are influenced by alterations in vibrational frequencies between the bound and the unbound states of a ligand, such as those described for the tautomers above. In general, if a bond order to an atom with the substitution decreases upon binding, it is the lighter isotope that binds better and a BIE of greater than 1.0 is observed. An inverse BIE or a BIE of less than 1.0 is indicative of an increase in bond order upon binding or tighter binding of the heavier isotope.

BIEs were measured for $^{18}O$ substitution at the 4'-position of OxyTPP. To monitor OxyTPP substituted with $^{18}O$, it was double labeled with $^{33}P$ at terminal phosphate of the pyrophosphate moiety. The OxyTPP with the lighter $^{16}O$ isotope was labeled with $^{32}P$. This allowed monitoring of $^{18}O$ versus $^{16}O$ OxyTPP in the reaction mixture by quantitating $^{33}P$ and $^{32}P$ radioactivity by scintillation counting. The double labeling scheme provided additional flexibility by switching the labeling pairs, i.e., by combining $^{18}O$ with $^{32}P$ and $^{16}O$ with $^{33}P$. The 4'-$^{18}O$ BIE was measured as a quotient of the ratio of light to heavy isotope of the bound and free forms of labeled OxyTPP. The riboswitch sequence used in the study is shown in FIG. 1B. It was obtained by in vitro transcription using T7 Polymerase using double stranded DNA containing the riboswitch sequence and the polymerase binding site cloned into the pUC19 vector. The [4'-$^{18}O$, $^{33}P$] and [4'-$^{18}O$, $^{33}P$] double labeled OxyTPPs were synthesized from $^{18}O$ and $^{16}O$ OxyT using TPK enzyme with $^{33}P$ and $^{32}P$ ATP labeled at the gamma position, respectively. Reverse pairs were obtained by using $^{33}P$ and $^{32}P$ labeled ATP with $^{16}O$ and $^{18}O$ OxyT, respectively, in the TPK reaction.

The protocol used for measuring BIE described elsewhere was modified.[22] BIE reactions were performed in 500 μl reaction volumes containing 100 mM HEPES pH 7.5, 100 mM KCl, 10 mM MgCl$_2$, 0.1-0.5 μM of OxyTPP and 2.0-5.0 μM of the TPP riboswitch. The $^{32}P$ and $^{33}P$ labeled OxyTPP were mixed in a 1:3.5 to 1:4.5 ratio for easy deconvolution of the scintillation spectrum to obtain $^{32}P$ and $^{33}P$ counts. The reaction mixtures were allowed to equilibrate for about 1-2 hours at 25° C. The reaction mixtures were applied to Microcon columns with 3000 KDa cutoff filters and centrifuged for about 30 minutes to allow half of the reaction to pass through the filter. Isovolumetric samples (usually about 200 μl) were taken from either side of the filter and transferred into scintillation vials containing 0.8 ml of H$_2$O and 10 ml OPTIMA GOLD scintillation fluid. The contents of the vials were mixed by vigorous shaking. The vials were counted for three cycles of 20 min per sample to obtain $^{32}P$ and $^{33}P$ counts. The isotope effect was calculated as the quotient of the ratio (light/heavy or $^{32}P/^{33}P$) of the bound OxyTPP and the ratio of free OxyTPP, quantitated using the following equation:

$$BIE = \frac{(((P32/P33) - 1))^{Above}}{(((P32/P33) - 1))^{Below}}$$

The $^{32}P$ to $^{33}P$ ratio quantitated above and below the filter were used to measure BIEs. The BIEs measured using double labeled OxyTPP contained contributions from both $^{18}O$ and $^{33}P$ substitutions. It was corrected for the $^{33}P$ BIE measured using singly substituted $^{33}P$ and $^{32}P$ OxyTPPs. To account for the systematic error in the experiment, controls were run using doubly labeled OxyTPP in the absence of the riboswitch. The BIE values were also corrected for $^{18}O$ enrichment, measured using a quadrupole time-of-flight (QTOF) mass spectrometer equipped with an electrospray ionization (ESI) source (see, e.g., Singh et al., ACS Chem. Biol., 2014, 9, 227-236), using the following relationship:

$$BIE_{corrected} = 1 + \frac{BIE_{observed} - 1}{1 - BIE_{observed}(1 - e)}$$

where e is the isotopic enrichment of the heavy sample. The equation assumes a negligible amount of heavy isotope in the light sample.

DFT Calculations for Calculating BIE for Tautomers:

The calculations for $^{18}O$ BIEs for OxyT were also performed using B3LYP functional and 6-31G (d, p) basis set implemented in Gaussian09. Structures were optimized and the frequencies were calculated using the optimized structures, which were then used to calculate BIEs using ISO-EFF98 software at 25° C. using the above mentioned scaling factor.

Solvation effects were examined by the self-consistent reaction field (SCRF) method in Gaussian09. The homogenous dielectric environment was simulated by a virtual solvent characterized the effective dielectric constants. The calculations were performed in argon, acetonitrile, and water, by using the dielectric constants recommended in Gaussian09. The radii used in the SCRF calculations were obtained by running calculations using the volume keyword.

Additional exemplary results are shown in FIGS. 5A and 5B.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of addi tional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein.

The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

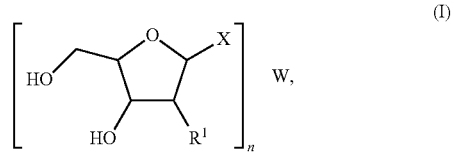

wherein:
R$^1$ is H or —OH;

X is of the formula:

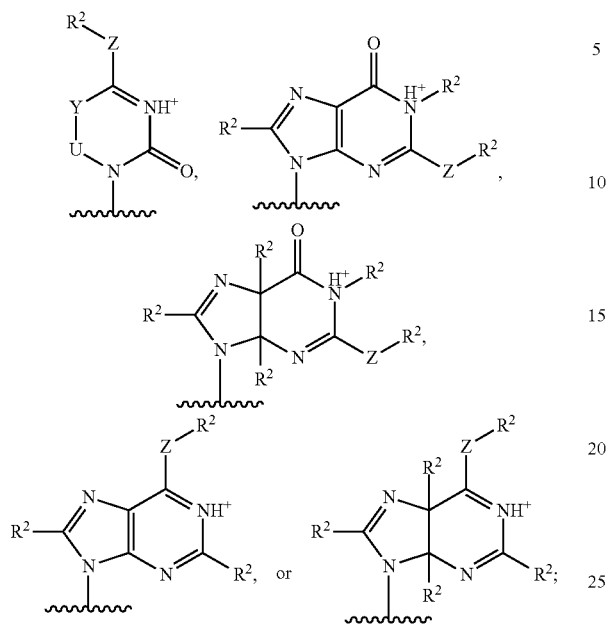

Y is —O—, —NR² — or —C(R²)₂—;
U is —O—, —NR² — or —C(R²)₂—;
Z is —O—, —S—, —NH—, or —C(R²)₂—;

each instance of R² is independently H, an electron-withdrawing group, or an electron-donating group; provided that at least one instance of R² is an electron-withdrawing group or an electron-donating group;

W is an anionic counterion; and n is 1, 2, or 3;

wherein the $pK_a$ of the compound is between 5.5 and 8.5, inclusive, and the $pK_a$ is a $pK_a$ at 25° C.

2. The compound of claim 1, wherein the compound is of the formula:

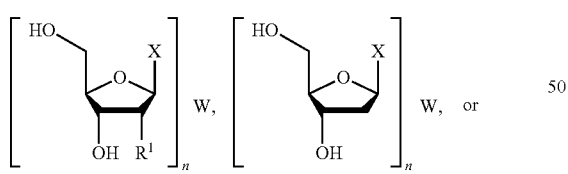

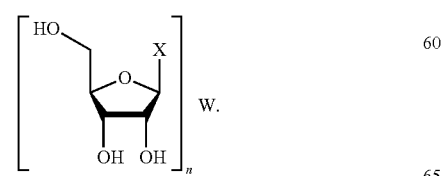

3. The compound of claim 1, wherein X is

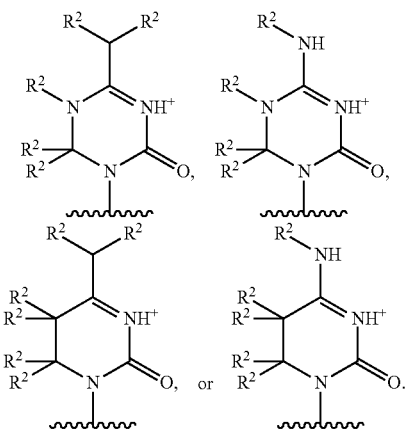

4. The compound of claim 1, wherein X is

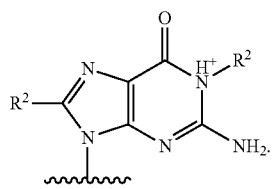

5. The compound of claim 1, wherein X is

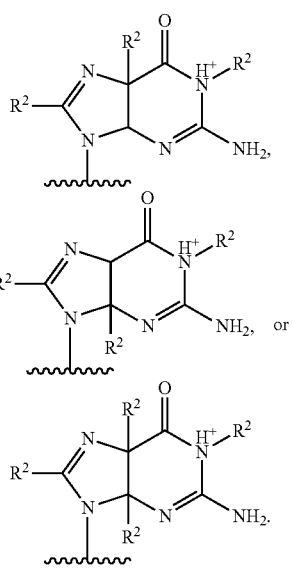

6. The compound of claim 1, wherein X is

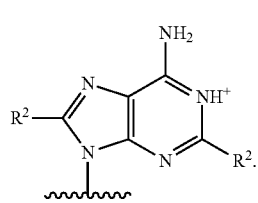

7. The compound of claim 1, wherein X is

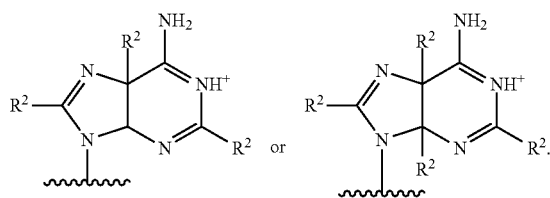

8. A pharmaceutical composition comprising a compound of claim 1 and optionally a pharmaceutically acceptable excipient.

9. A method of treating a viral infection in a subject in need thereof, the method comprising administering to the subject in need thereof an effective amount of a compound of claim 1.

10. A method of increasing the mutation rate of a RNA or DNA of a virus, the method comprising contacting the virus with an effective amount of a compound of claim 1.

11. A method of killing a virus, the method comprising contacting the virus with an effective amount of a compound of claim 1.

12. A method of inhibiting the replication of a virus, the method comprising contacting the virus with an effective amount of a compound of claim 1.

13. A method of treating cancer in a subject in need thereof, the method comprising administering to the subject in need thereof an effective amount of a compound of claim 1.

14. A method of increasing the mutation rate of a RNA and/or DNA of a cancer cell, the method comprising contacting the cancer cell with an effective amount of a compound of claim 1.

15. A method of inducing apoptosis of a cancer cell, the method comprising contacting the cancer cell with an effective amount of a compound of claim 1.

16. A method of decreasing DNA methylation in a cancer cell, the method comprising contacting the cancer cell with an effective amount of a compound of claim 1.

17. A kit comprising:
a compound of claim 1; and
instructions for using the compound or pharmaceutical composition.

18. The compound of claim 1, wherein X is:

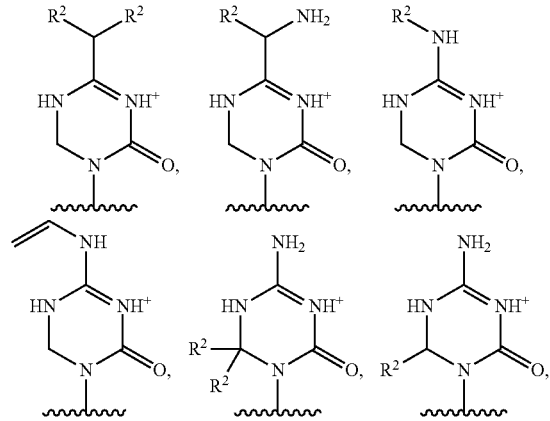

-continued

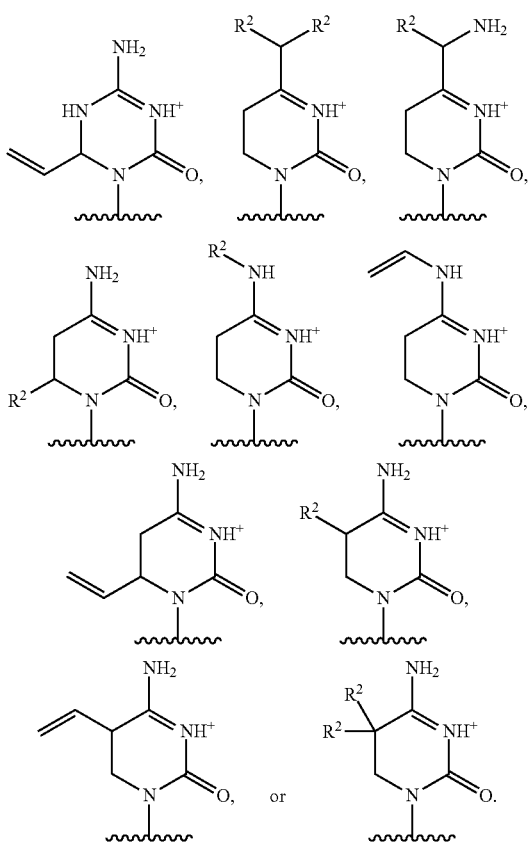

19. The compound of claim 1, wherein X is:

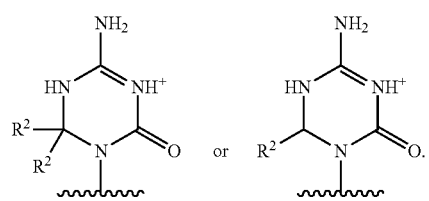

20. The compound of claim 1, wherein X is:

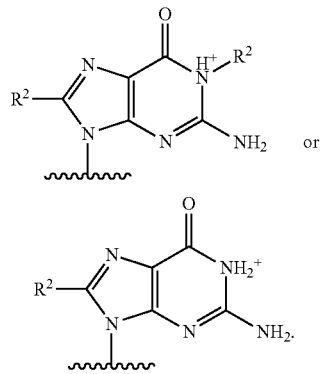

21. The compound of claim 1, wherein X is:

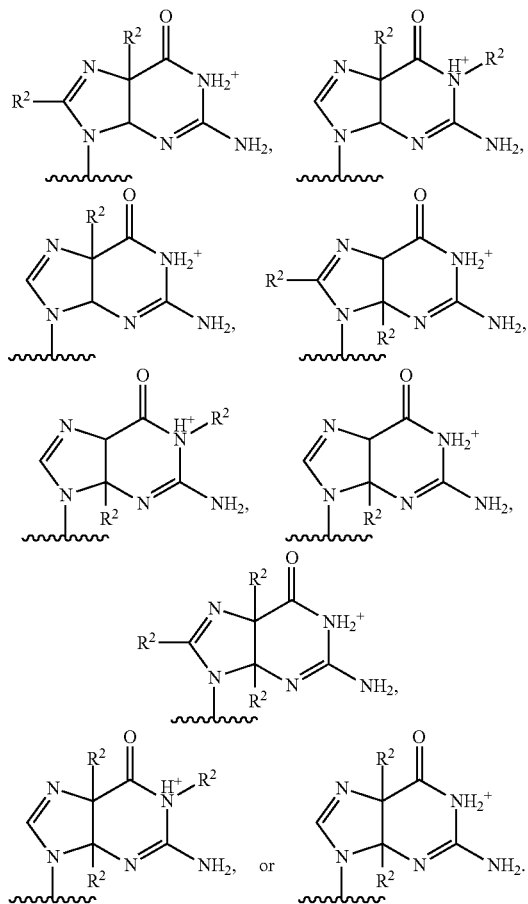

22. The compound of claim 1, wherein X is:

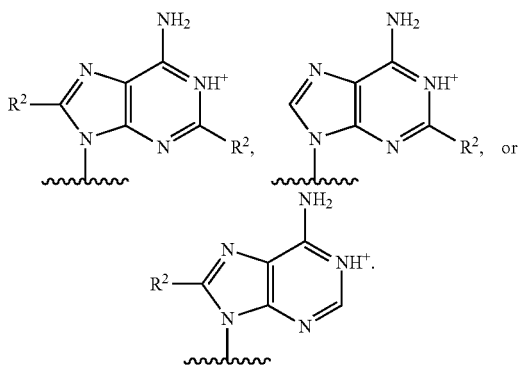

23. The compound of claim 1, wherein X is:

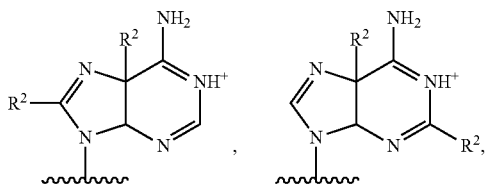

-continued

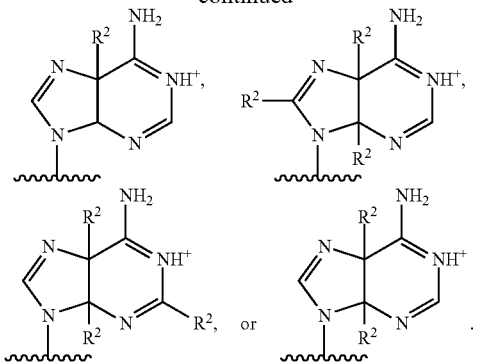

24. The compound of claim 1, wherein Z is —NH—.
25. The compound of claim 1, wherein Z is -C(R$^2$)$_2$-.
26. The compound of claim 1, wherein W is F$^-$, Cl$^-$, Br$^-$, I$^-$, NO$_3^-$, ClO$_4^-$, OH$^-$, H$_2$PO$_4^-$, HPO$_4^{2-}$, PO$_4^{3-}$, HSO$_4^-$, SO$_4^{2-}$, OTf$^-$, OTs$^-$, OMs$^-$, OAc$^-$, OBz$^-$, BF$_4^-$, PF$_4^-$, PF$_6^-$, AsF$_6^-$, or SbF$_6^-$.
27. The compound of claim 1, wherein n is 1.
28. The compound of claim 1, wherein each of the electron-withdrawing group and electron-donating group is independently:
 if attached to a carbon atom: halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, —OC(=O)N(R$^a$)$_2$, —SeR$^a$, —N(R$^a$)$_3^+$, —O—OR$^a$, —N=NR$^a$, —N$_3$, —S(=O)R$^a$, —S(=O)OR$^a$, —S(=O)N(R$^a$)$_2$, —S(=O)$_2$R$^a$, —S(=O)$_2$OR$^a$, —S(=O)$_2$N(R$^a$)$_2$, —NO, or —C(=O)—halide; or
 if attached to a nitrogen atom: substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, or a nitrogen protecting group;
 wherein each instance of R$^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted, heterocyclic ring, or substituted or unsubstituted, heteroaryl ring.
29. The compound of claim 1, wherein each of the electron-withdrawing group and electron-donating group, if attached to a carbon atom, is independently F, Cl, or —OH.

30. The compound of claim 1, wherein the $pK_a$ is between 6.5 and 7.5, inclusive.

31. The pharmaceutical composition of claim 8 further comprising an additional pharmaceutical agent, wherein the additional pharmaceutical agent is an anticancer agent.

32. The method of claim 13, wherein the cancer is a cancer with a mutator phenotype.

* * * * *

SEQUENCE LISTING

<160> NUMBER OF SEQ ID NOS: 3

<210> SEQ ID NO 1
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 1
cgtgatcatg cgcagactga catcatgtgt aaaacgacgg ccagtgaatt gga          53

<210> SEQ ID NO 2
<211> LENGTH: 28
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by a phospho-hexylamino linker

<400> SEQUENCE: 2
cagctatgac catgattcag tggaagac                                       28

<210> SEQ ID NO 3
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by a phospho-hexylamino linker

<400> SEQUENCE: 3
cgtgatcatg cgcagactga catcatgtg                                      29